US007582292B2

(12) United States Patent
Wilkison et al.

(10) Patent No.: US 7,582,292 B2
(45) Date of Patent: Sep. 1, 2009

(54) ADIPOSE TISSUE DERIVED STROMAL CELLS FOR THE TREATMENT OF NEUROLOGICAL DISORDERS

(75) Inventors: William O. Wilkison, Bahama, NC (US); Jeffrey M. Gimble, Baton Rouge, LA (US); Padmavathy Vanguri, Cockeysville, MD (US)

(73) Assignee: Artecel, Inc., Bethesda, MD (US)

( * ) Notice: Subject to any disclaimer, the term of this patent is extended or adjusted under 35 U.S.C. 154(b) by 0 days.

(21) Appl. No.: 11/286,900

(22) Filed: Nov. 23, 2005

(65) Prior Publication Data

US 2007/0104697 A1    May 10, 2007

Related U.S. Application Data

(63) Continuation-in-part of application No. 09/793,173, filed on Feb. 26, 2001, now Pat. No. 7,078,230.

(60) Provisional application No. 60/185,338, filed on Feb. 26, 2000.

(51) Int. Cl.
  *A01N 63/00*  (2006.01)
  *C12N 5/00*  (2006.01)
  *C12N 5/06*  (2006.01)
  *C12N 5/08*  (2006.01)
  *C12N 5/16*  (2006.01)

(52) U.S. Cl. .................. 424/93.7; 424/93.1; 424/93.21; 435/335; 435/366; 435/368; 435/377

(58) Field of Classification Search ........................ None
See application file for complete search history.

(56) References Cited

U.S. PATENT DOCUMENTS

| 5,041,138 | A | 8/1991 | Vacanti et al. |
| 5,144,016 | A | 9/1992 | Skjak-Braek et al. |
| 5,486,359 | A | 1/1996 | Caplan et al. |
| 5,516,532 | A | 5/1996 | Atala et al. |
| 5,536,656 | A | 7/1996 | Kemp et al. |
| 5,709,854 | A | 1/1998 | Griffith-Cima et al. |
| 5,723,331 | A | 3/1998 | Tubo et al. |
| 5,736,372 | A | 4/1998 | Vacanti et al. |
| 5,736,396 | A | 4/1998 | Bruder et al. |
| 5,741,685 | A | 4/1998 | Vacanti et al. |
| 5,759,830 | A | 6/1998 | Vacanti et al. |
| 5,770,193 | A | 6/1998 | Vacanti et al. |
| 5,770,417 | A | 6/1998 | Vacanti et al. |
| 5,786,207 | A | 7/1998 | Katz et al. |
| 5,804,178 | A | 9/1998 | Vacanti et al. |
| 5,811,094 | A | 9/1998 | Caplan et al. |
| 5,827,735 | A | 10/1998 | Young et al. |
| 5,855,610 | A | 1/1999 | Vacanti et al. |
| 5,863,531 | A | 1/1999 | Naughton et al. |
| 5,879,940 | A | 3/1999 | Torok-Storb et al. |
| 5,902,741 | A | 5/1999 | Purchio et al. |
| 5,908,784 | A | 6/1999 | Johnstone et al. |
| 5,942,225 | A | 8/1999 | Bruder et al. |
| 5,944,754 | A | 8/1999 | Vacanti |
| 6,027,744 | A | 2/2000 | Vacanti et al. |
| 6,030,836 | A | 2/2000 | Thiede et al. |
| 6,103,522 | A | 8/2000 | Torok-Storb et al. |
| 6,123,727 | A | 9/2000 | Vacanti et al. |
| 6,139,574 | A | 10/2000 | Vacanti et al. |
| 6,143,501 | A | 11/2000 | Sittinger et al. |
| 6,153,432 | A | 11/2000 | Halvorsen et al. |
| 6,200,606 | B1 | 3/2001 | Peterson et al. |
| 6,391,297 | B1 | 5/2002 | Halvorsen |
| 6,429,013 | B1 | 8/2002 | Halvorsen et al. |
| 6,936,418 | B2 | 8/2005 | Dutreix et al. .................. 435/6 |
| 7,078,230 | B2 | 7/2006 | Wilkison et al. ............. 435/325 |

FOREIGN PATENT DOCUMENTS

| WO | WO 96/02662 A1 | 2/1996 |
| WO | WO 98/20731 A1 | 5/1998 |
| WO | WO 99/53286 A2 | 2/1999 |
| WO | WO 99/28444 A1 | 6/1999 |
| WO | WO 99/61587 A1 | 12/1999 |
| WO | WO 00/44882 A2 | 8/2000 |
| WO | WO 00/53795 A1 | 9/2000 |
| WO | WO 01/21767 A2 | 3/2001 |

OTHER PUBLICATIONS

Björklund and Lindvall, Nature Neuroscience 3(6):537-544, Jun. 2000.*
Bain et al., "Embryonic Stem Cells Express Neuronal Properties in Vitro," Develop. Biol., 168:342-357, 1995.
Beresford et al., "Evidence for an inverse relationship between the differentiation of adipocytic and osteogenic cells in rat marrow stromal cell cultures," *J. Cell Sci.*, 1992, 99:131.
Bjornson, "Turning Brain into Blood: A Hematopoietic Fate Adopted by Adult Neural Stem Cells in Vivo," *Science*, 1999, 283:534-537.
Bruder et al., "Mesenchymal Stem Cells in Bone Development, Bone Repair, and Skeletal Regeneration Therapy," *J. Cell Biochem.*, 1997, 56:283-294.
Burris et al., A Novel Method for Analysis of Nuclear Receptor Function at Natural Promoters: Peroxisome Proliferator-Activated Receptor γ Agonist Actions on a P2 Gene Expression Detected Using Branched DNA Messenger RNA Quantitation, *Molecular Endocrinology*, 1999, 13, 3, 410.

(Continued)

*Primary Examiner*—John Ulm
*Assistant Examiner*—Stacey Macfarlane
(74) *Attorney, Agent, or Firm*—Seed IP Law Group PLLC

(57) ABSTRACT

The present invention relates to a treatment of neural injury and neurodegenerative diseases. Also included in the present invention is the use of adipose tissue derived stromal cells for the treatment of neural injury (stroke, traumatic brain injury, spinal cord injury) and neurodegeneration (i.e. Parkinson's disease).

17 Claims, 2 Drawing Sheets

OTHER PUBLICATIONS

Dani et al., "Differentiation of embryonic stem cells into adipocytes in vitro," *J. Cell Sci.*, 1997, 110:1279-1285.

Darmon et al., "5-Azacytidine Is Able To Induce The Conversion Of Teratocarcinoma-Derived Mesenchymal Cells Into Epithelial Cells," *The IMBO Journal*, 1984, 3:961-967.

Dorheim et al., "Osteoblastic Gene Expression During Adiopogensis in Hematopoietic Supporting Murine Bone Marrow Stromal Cells," *J. Cell Physiol.*, 1993, 154:317-328.

Erikson et al., "Chondrogenic Potential of Adipose Tissue-Derived Stromal Cells in Vitro and in Vivo," 2002, *Biochem. Biophys. Res. Comm.* 290(2):763-769.

Feigin et al., "Recent Advances in Huntington's Disease: Implication for Experimental Therapeutics," 2002, *Curr. Opin. Neurol.* 15:483-489.

Gimble, Jeffrey Martin, "The Function of Adipocytes in the Bone Marrow Stroma," *The New* Biologist, 1990, 2, 4, 304.

Gimble et al., "Adipogensis in a murine bone marrow stromal cell line capable of supporting B lineage lymphocyte growth and proliferation: biochemical and molecular characterization," *Eur. J. Immunol.*, 1990, 20:379-387.

Gimble et al., "Characterization of Murine Bone Marrow and Spleen-Derived Stromal Cells: Analysis of Leukocyte Marker and Growth Factor mRNA transcript Levels," *Blood*, 1989, 74:303-311.

Gimble et al., "The Function of Adipocytes in the Bone Marrow Stromal: An Update," *Bone*, 1996, 19:421-428.

Gimble et al., "Nuclear Hormone Receptors and Adipogenesis," *Critical Reviews in Eukaryotic Gene Expressions*, 1998, 8(2), 141.

Gimble et al., "Adipocyte Biology of the Bone," *Adipocyte Biology and Hormone Signaling*, IOS Press, The Netherlands, 2000, 231.

Gronthos et al., "The STRO-1+Fraction of Adult Human Bone Marrow Contains the Osteogenic Precursors," *Blood*, 1994, 84:4164-4173.

Gronthos et al., "Surface Protein Characterization of Human Adipose Tissue-Derived Stromal Cells," *Journal of Cellular Physiology*, 2001, 9999, 1.

Halliday et al., Alzheimer's Disease and Inflammation: A Review of Cellular and Therapeutic Mechanisms, 2000, *Clin. Exp. Pharmacol. Physiol.* 27:1-8.

Halvorsen et al., "Adipose-derived stromal cells—their utility and potential in bone formation," 2000, *Int. J. Obes. Relat. Metab. Disord.* Suppl. 4:S41-44.

Halvorsen et al., "Extracellular matrix mineralization and osteoblast gene expression by human adipose tissue-derived stromal cells," 2001, *Tissue Eng.* 7(6):729-741.

Halvorsen et al., "Thiazolidinediones and glucocorticoids synergistically induce differentiation of human adipose tissue stromal cells: biochemical, cellular, and molecular analysis," 2001, *Metabolism* 50(4):407-413.

Jakoby & Pastan, "Basic Methods" and "Media and Growth Requirements," *Methods in Enzymology, Cell Culture*, vol. LVIII, pp. 62-72, 1979.

Jackson et al., "Hematopoietic potential of stem cells isolated from murine skeletal muscle," *PNAS*, 1999, 96:14482-14486.

Johnson RS, "Targeting of nonexpressed Genes in Embryonic Stem Cells Via Homologous Recombination," *Science*, 1989, 245:1234-1236.

Kang et al., "Neurogeneis of Rhesus Adipose Stromal Cells," 1999, *J. Cell Sci.* 117:4289-4299.

Kang et al., "Improvement of Neurological Deficits by Intracerebral Transplantation of Human Adipose Tissue-Derived Stromal Cells After Cerebral Ischemia in Rats," 2003, *Exp. Neurol.* 183:355-366.

Kim et al., "Effect of Partial Hepatectomy on in Vivo Engraftment After Intravenous Administration of Human Adipose Tissue Stroma Cells in Mouse," 2003, 23:424-431.

Kopen et al., "Marrow stromal cells migrate throughout forebrain and cerebellum, and they differentiate into astrocytes after injection into neonatal mouse brains," 1999, *PNAS*, 96:10711-10716.

Lee et al., "Normal B Cell Precursors Responsive To Recombinant Murine IL-7 and Inhibition of IL-7 Activity by Transforming Growth Factor-$\beta^1$," 1989, *J. Immunol.*, 142:3875-3883.

McDonald et al., "Transplanted embryonic stem cells survive, differentiate and promote recovery in injured rat spinal cord," 1999, *Nature Med.*, 5(12):1410-1412.

Medina et al., "Suppression of B Lymphopoeisis during Normal Pregnancy," 1993, *J. Exp. Med.* 178:1507-1515.

Mizuno, "The Myogenic Potential of Human Processes Lipoaspirates—Part I: Morphological, immunohistochemical analysis and gene expression," 2001, *J. Jpn. P.R.S.* 21, 427.

Mizuno et al., "Myogenic Differentiation by Human Processed Lipoaspirate Cells," 2002, *Plastic and Reconstructive Surgery* 109, 1, 199.

Moore et al., "In Vitro Colony Formation by Normal and Leukemic Human Hematopoietic Cells: characterization of the Colony-Forming Cells [1,2]," 1973, *J. Natl. Cancer Inst.* 50:603-623.

O'Shea, "Embryonic Stem Cell Models of Development," 1999, *Anat. Rec.* 257:32-41.

Petersen et al., "Bone Marrow as a Potential Source of Hepatic Oval Cells," 1999, *Science* 284:1168-1170.

Pereira et al., "Marrow stromal cells as a source of progenitor cells for nonhematopoietic tissues in transgenic mice with a phenotype of osteogenesis imperfecta," 1998, *PNAS*, 95:1142-1147.

Pietrangeli et al., "Stromal cell lines which support lumphocyte growth: characterization, sensitivity to radiation and responsiveness to growth factors," 1988, *Eur. J. Immunol.* 18:863-872.

Prockop, "Marrow Stromal Cells as Stem Cells for Continual Renewal of Nonhematopoietic Tissues and as Potential Vectors for Gene Therapy," 1998, *J. Cell Biochem. Suppl.* 30-31:284-285.

Quesenberry et al., "Correlates between Hematopoiesis and Neuropoiesis: Neural Stem Cells," 1999, *J. Neurotrauma* 16:661-666.

Remoncourt et al., "Neurons derived in vitro from ES cells express homeoproteins characteristic of motoneurons and interneurons," 1998, 79:185-197.

Safford et al., "Neurogenic differentiation of murine and human adipose-derived stromal cells," 2002, *Biochem. Biophys. Res. Commun.* 294(2):371-379.

Safford et al., "Characterization of neuronal/glial differentiation of murine adipose-derived adult stromal cells," 2004, *Exp. Neurol.* 187:319-328.

Saladin et al., "Differential Regulation of Peroxisome Proliferator Activated Receptor γ1 (PPARγ1) and PPARγ2 Messenger RNA Expression in the Early Stages of Adipogenesis[1]," 1999, *Cell Growth & Differentiation* 10,43.

Sanchez-Ramos et al., "Adult Bone Marrow Stromal Cells Differentiate into Neural Cells in Vitro," 2000, *Exp. Neurology* 164:247-256.

Sen et al., "Adipogenic potential of human adipose derived stromal cells from multiple donors is heterogeneous," 2001, *J. Cell Biochem.* 81(2):312-319.

Steece-Collier et al., "Etiology of Parkinson's Disease: genetics and environmental revisited," 2002, *Proc. Natl. Acad. Sci. USA* 99(22):13972-13974.

Svendson & Smith, "New prospects for human stem-cell therapy in the nervous," 1999, *Trends Neurosci.* 22:357-364.

Till & McCuloch, "A Direct Measurement of the Radiation Sensitivity of Normal Mouse Bone Marrow Cells[1]," 1961, *Rad. Res.* 14:213-222.

Woodbury et al., "Adult Rat and Human Bone Marrow Stromal Cells Differentiate Into Neurons," 2000, *J. Neuroscience Research* 61:364-370.

Trentin, "Transplanation: The State of the Art," 1965, *Cardiovasc. Res. Cent. Bull.* 4:38-44.

Yang et al., "Adipose tissue-derived stromal cells express neuronal phenotypes," 2004, *Clin. Med. J.* 116(3):425-429.

Zuk et al., "Multilineage Cells from Human Adipose Tissue: Implication for Cell-Based Therapies," 2001, *Tissue Engineering* 7, 2, 211.

Zuk et al., "Human adipose tissue is a source of multipotent stem cells," 2002, *Mol. Biol. Cell.* 13(12):4279-4295.

Gimble, Jeffrey M., "Adipose tissue-derived therapeutics," *Expert Opin. Biol. Ther.* 3(5):705-713, 2003.

\* cited by examiner

ADIPOSE TISSUE DERIVED STROMAL CELLS FOR THE TREATMENT OF NEUROLOGICAL DISORDERS

CROSS-REFERENCE TO RELATED APPLICATIONS

The present application is a continuation-in-part of U.S. patent application Ser. No. 09/793,173, filed on Feb. 26, 2001, which claims the benefit under 35 U.S.C. § 119(e) to U.S. Provisional Application No. 60/185,338, filed Feb. 26, 2000, all of which are herein incorporated by reference in their entirety.

BACKGROUND OF THE INVENTION

A stem cell must meet the following criteria: (1) ability of a clonal stem cell population to self-renew; (2) ability of a clonal stem cell population to generate a new, terminally differentiated cell type in vitro; (3) ability of a clonal stem cell population to replace an absent terminally differentiated cell population when transplanted into an animal depleted of its own natural cells.

The neonatal period in human development is characterized by the presence of "stem" cells with the potential to develop along multiple differentiation pathways. The terminal differentiation of these cells is determined by cytokine and hormonal cues which co-ordinate organogenesis and tissue architecture. Murine embryonic stem (ES) cells have been isolated and studied extensively in vitro and in vivo. Using exogenous stimuli in vitro, investigators have induced ES cell differentiation along multiple lineage pathways. These pathways include neuronal, B lineage lymphoid, and adipocytes (Dani et al., 1997, J. Cell Sci. 110:1279; Remoncourt et al., 1998, Mech Dev 79:185; O'Shea, 1999, Anat. Rec. 257:32). The ES cells have been manipulated in vivo by homologous recombination techniques to generate gene specific null or "knock-out" mice (Johnson, 1989, Science 245:1234). Once ES cell clones lacking a specific gene are isolated, they are transplanted into a fertilized murine zygote. The progeny of this isolated ES cell can develop into any and all murine tissues in a coordinated manner.

Multipotential stem cells exist in tissues of the adult organism. The best characterized example of a "stem cell" is the hematopoietic progenitor isolated from the bone marrow and peripheral blood. Seminal studies by Trentin and colleagues (Trentin, 1965, Cardiovasc. Res. Cent. Bull 4:38; Till & McCulloch, 1961, Rad. Res. 14:213) examined lethally irradiated mice. In the absence of treatment, these animals died because they failed to replenish their circulating blood cells; however, transplantation of bone marrow cells from syngeneic donor animals rescued the host animal. The donor cells were responsible for repopulating all of the circulating blood cells. A wealth of elegant studies have gone on to demonstrate that donation of a finite number of undifferentiated hematopoietic stem cells is capable of regenerating each of the eight or more different blood cell lineages in a host animal. This work has provided the basis for bone marrow transplantation, a widely accepted therapeutic modality for cancer and inborn errors of metabolism. Thus, hematopoietic stem cells remain present in normal human bone marrow throughout life; they are not limited to the neonatal period.

There is exciting new evidence that hematopoietic progenitors may not be limited to the bone marrow microenvironment. Investigators at the University of Calgary have examined neuronal stem cells, which routinely differentiate along neuronal cell lineage pathways. When these cells were transplanted into lethally irradiated hosts, the investigators detected the presence of donor cell markers in newly produced myeloid and lymphoid cells (Bjornson, 1999, Science 283:534). Investigators at the Baylor College of Medicine have performed similar studies using satellite cells isolated from murine skeletal muscle (Jackson et al., 1999, PNAS 96:14482). When these muscle-derived cells were transplanted into lethally irradiated hosts, the investigators detected the presence of the muscle gene markers in all blood cell lineages. Together, these studies indicate that neuronal and muscle tissues contain stem cells capable of hematopoietic differentiation. This suggests that sites other than the bone marrow may provide a renewable source of hematopoietic progenitors with potential application to human disease therapy (Quesenberry et al., 1999, J. Neurotrauma 16:661: Scheffler et al., 1999, Trends Neurosci 22:348; Svendson & Smith, 1999, Trends Neurosci 22:357).

Just as neuronal and muscle cells are capable of regenerating the irradiated bone marrow, bone marrow derived cells are capable of repopulating other organ sites. When bone marrow derived hematopoietic and stromal cells are transplanted into an animal with an injured liver, they are capable of regenerating hepatic oval cells in the host animal (Petersen et al., 1999, Science 284:1168). Similarly, when labeled bone marrow stromal cells are implanted into the lateral ventricle of a neonatal mouse, they were capable of differentiating into mature astrocytes (Kopen et al., 1999, PNAS 96:10711). Indeed, when bone marrow stromal cells are transplanted intraperitoneally into mice, they are detected throughout the organs of the host animal, including the spleen, lung, bone marrow, bone, cartilage, and skin (Pereira et al., 1998, PNAS 95:1142). These studies suggest that the bone marrow stromal cell is capable of differentiating into lineages different from their original origin (Kopen et al., 1999, PNAS 96:10711).

The recent development of entire organisms from a single donor cell is consistent with this hypothesis. For example, the "Dolly" experiment showed that cells isolated from an ovine mammary gland could develop into a mature sheep. In similar murine studies, cells derived from the corpus luteum of the ovary could develop into a mature mouse. These studies suggest that stem cells with the ability to differentiate into any and all cell types continue to exist in the adult organism. Thus, "embryonic" stem cells may be retained throughout the life of an individual.

The adult bone marrow microenvironment is the potential source for these hypothetical stem cells. Cells isolated from the adult marrow are referred to by a variety of names, including stromal cells, stromal stem cells, mesenchymal stem cells (MSCs), mesenchymal fibroblasts, reticular-endothelial cells, and Westen-Bainton cells (Gimble et al., 1996, Bone 19:421). In vitro studies have determined that these cells can differentiate along multiple mesenchymal or mesodermal lineages which include, but are not limited to, adipocytes (fat cells) (Gimble et al., 1990, Eur J. Immunol 20:379), Chondrocytes (Bruder et al., 1994, J. Cell Biochem. 56:283), hematopoietic supporting cells (Pietrangeli et al., 1988, Eur. J. Immunol. 18:863), skeletal muscle myocytes (Prockop, 1998, J. Cell Biochem Suppl. 30-31:284-5), smooth muscle myocytes (Charbord et al., 2000, J. Hematother. Stem Cell Res. 9:935-43), and osteoblasts (Beresford et al., 1992, J. Cell Sci. 99:131; Dorheim et al., 1993, J. Cell Physiol. 154:317). In addition, bone marrow stromal cells display the ability to differentiate into astrocytes (Kopen et al., 1999, PNAS 96:10711) and hepatic oval cells (Petersen et al., 1999, Science 284:1168). Based on these findings, the bone marrow has been proposed as a source of stromal stem cells for regeneration of bone, cartilage, muscle, adipose tissue, liver, neuronal, and other tissues. However, extraction of bone marrow stromal cells presents a high level of risk and discomfort to the patient.

In contrast, adult human extramedullary adipose tissue-derived stromal cells represent a stromal stem cell source that can be harvested routinely with minimal risk or discomfort to the patient. Pathologic evidence suggests that adipose-derived stromal cells are capable of differentiation along multiple lineage pathways. The most common soft tissue tumors, liposarcomas, develop from adipocyte-like cells. Soft tissue tumors of mixed origin are relatively common. These tumors may include elements of adipose tissue, muscle (smooth or skeletal), cartilage, and/or bone. In patients with a rare condition known as progressive osseous heteroplasia, subcutaneous adipocytes form bone for unknown reasons.

Recent studies have demonstrated the specific ability of bone marrow-derived stromal cells to undergo neuronal differentiation in vitro (Woodbury et al., 2000, J. Neuroscience Research 61:364; Sanchez-Ramos et al., 2000, Exp. Neurology 164:247). In these investigations, treatment of bone marrow stromal cells with antioxidants, epidermal growth factor (EGF), or brain derived neurotrophic factor (BDNF) induced the cells to undergo morphologic changes consistent with neuronal differentiation, i.e., the extension of long cell processes terminating in growth cones and filopodia (Woodbury et al., 2000, J. Neuroscience Research 61:364; Sanchez-Ramos et al., 2000, Exp. Neurology 164:247). In addition, these agents induced the expression of neuronal specific protein including nestin, neuron-specific enolase (NSE), neurofilament M (NF-M), NeuN, and the nerve growth factor receptor trkA (Woodbury et al., 2000, J. Neuroscience Research 61:364; Sanchez-Ramos et al., 2000, Exp. Neurology 164: 247).

Most central nervous system (CNS) injuries including stroke, trauma, hypoxia-ischemia, multiple sclerosis, seizure, infection, and poisoning, directly or indirectly involve a disruption of blood supply to the CNS. These injuries share the same common pathologic process of rapid cerebral edema leading to irreversible brain damage and eventually to brain cell death.

Stroke results in the destruction of brain tissue as a result of intracerebral hemorrhage or infarction. Stroke may be caused by reduced blood flow or ischemia that results in deficient blood supply and death of tissues in one area of the brain (infarction). The causes of ischemic stroke include blood clots that form in the blood vessels in the brain (thrombus) and blood clots or pieces of atherosclerotic plaque or other material that travel to the brain from another location (emboli). Bleeding (hemorrhage) within the brain may also cause symptoms that mimic stroke.

The CNS tissue is highly dependent on blood supply and is very vulnerable to interruption of blood supply. Even a brief interruption of the blood flow to the CNS can cause neurological deficit. The brain is believed to tolerate complete interruption of blood flow for a maximum of about 5 to 10 minutes. It has been observed that after blood flow is restored to areas of the brain that have suffered an ischemic injury, secondary hemodynamic disturbances have long lasting effects that interfere with the ability of the blood to supply oxygen to CNS tissues. Similarly, interruption of the blood flow to the spinal cord, for even short periods of time, can result in paralysis.

The majority of stroke cases are the result of ischemia (low tissue oxygen supply) due to blockages to the blood vessels serving CNS. These blockages arise from narrowing of the vessels due to build up of atherosclerotic plaques usually in combination with occlusion due to entrapment at the narrowed region of small clots of aggregated platelets (thrombus). The other cases of strokes arise from hemorrhagic (bleeding) events (e.g. intracerebral hemorrhage, subarachnoid hemorrhage) in which a blood vessel within the CNS ruptures leading to mechanical and ischemic damage.

Recognition of the "ischemic penumbra," a region of reduced cerebral blood flow in which cell death might be prevented, has focused attention on treatments that might minimize or reverse brain damage when the treatments are administered soon after stroke onset. To date, several classes of neuroprotective compounds have been investigated for treatment of acute stroke. They have included calcium channel antagonists, N-methyl-D-aspartate (NMDA) receptor antagonists, free radical scavengers, anti-intercellular adhesion molecule 1 antibody, GM-1 ganglioside, γ-aminobutyric acid agonists, and sodium channel antagonists, among others. Results of various trials have yielded disappointing efficacy data and some evidence of safety problems, including increased mortality or psychotic effects which resulted in the early termination of the trials.

Each year about 700,000 people are afflicted by stroke in the United States. Stroke is the third highest cause of death and the leading cause of serious long term disability. The incidence of stroke increases dramatically with age with the highest risk occurring in persons at least 75 years old. Existing therapies rely on prompt treatment (i.e within minutes/hours) following a stroke but there is presently no effective or beneficial therapy that can be applied at later time points (days/weeks) after the onset of stroke. Thus there remains a large unmet need for treatments that improve neurological function after the onset of stroke.

BRIEF SUMMARY OF THE INVENTION

The present invention includes a method of treating a mammal suffering from a disease, disorder or condition of the central nervous system (CNS). Preferably, the disease, disorder or condition of the CNS is stroke. The treatment includes the steps of culturing an adipose tissue derived stromal cell and administering the adipose tissue derived stromal cell to a mammal in need thereof. Preferably, the mammal is a human.

In one aspect, the administered adipose tissue derived stromal cell induces neurorestorative pathways in the brain of the mammal. In another aspect, the adipose tissue derived stromal cell induces the generation of new neurons in the brain of the mammal.

The invention also provides a method of activating the differentiation of neural cells in an injured brain. This method comprises the steps of administering an adipose tissue derived stromal cell adjacent to the injured brain cells by way of intravascular (intra-arterial, intravenous) administration of the adipose tissue derived stromal cells to the mammal. Preferably, the administered adipose tissue derived stromal cell activates endogenous CNS stem cells to differentiate into neurons.

The cells of the present invention can be cultured in a neuronal differentiation medium prior to administration into a mammal. The cells can be cultured in the presence of a neurotrophin, prior to administering the cells to the mammal. The cells can be injected either directly into the brain, into the internal carotid artery or into a femoral vein of the mammal. Following administration of the cells to the mammal, behavioral and functional tests to identify therapeutic outcome can be tested. The disclosure presented herein demonstrates that treatment of stroke, spinal cord injury, or traumatic brain injury, with adipose tissue derived stromal cells significantly reduces functional deficits exhibited by the mammal as the result of undergoing conditions of stroke, spinal cord injury, or traumatic brain injury.

The invention also relates to a method of treating a human patient having a disease, disorder or condition of the CNS. The method comprises obtaining adipose tissue derived stromal cells from a donor and administering the isolated stromal cells to the CNS of the human patient, wherein the presence of the isolated stromal cells in the CNS effects treatment of the disease, disorder or condition. In one aspect, the presence of the isolated stromal cells in the CNS of the human patient does not induce an immune response against the stromal cells.

In another aspect, the administered stromal cell secretes a factor in the CNS of the patient. The factor is selected from the group consisting of a growth factor, a trophic factor and a cytokine. In a further aspect, the secreted factor is selected from the group consisting of leukemia inhibitory factor (LIF), brain-derived neurotrophic factor (BDNF), epidermal growth factor receptor (EGF), basic fibroblast growth factor (bFGF), FGF-6, glial-derived neurotrophic factor (GDNF), granulocyte colony-stimulating factor (GCSF), hepatocyte growth factor (HGF), IFN-γ, insulin-like growth factor binding protein (IGFBP-2), IGFBP-6, IL-1ra, IL-6, IL-8, monocyte chemotactic protein (MCP-1), mononuclear phagocyte colony-stimulating factor (M-CSF), neurotrophic factors (NT3), tissue inhibitor of metalloproteinases (TIMP-1), TIMP-2, tumor necrosis factor (TNF-β), vascular endothelial growth factor (VEGF), VEGF-D, urokinase plasminogen activator receptor (uPAR), bone morphogenetic protein 4 (BMP4), IL1-a, IL-3, leptin, stem cell factor (SCF), stromal cell-derived factor-1 (SDF-1), platelet derived growth factor-BB (PDGFBB), transforming growth factors beta (TGFβ-1) and TGFβ-3.

In another aspect, the stromal cells are administered to the mammal at an adjacent site to the site of injury. In one aspect, following administering the stromal cells to the mammal, the stromal cells migrate to the site of injury. In another aspect, the administered stromal cells express phenotypes of parenchymal cells. In a further aspect, the stromal cells present in the CNS activate the proliferation of neighboring cells. Preferably, the neighboring cells are astrocytes. More preferably, the neighboring cells are neural progenitor cells. Even more preferably, the neighboring cells are astrocytes and neural progenitor cells.

In another aspect, the stromal cells administered to the CNS remain present or replicate in the CNS.

In a further aspect, prior to administering the isolated stromal cells, the cells are cultured in vitro. Preferably, the cells are pre-differentiated by culturing the cells in a differentiation medium, whereby the stromal cells differentiate and acquire the phenotypic characteristics of neuronal cells.

In yet another aspect, prior to administration of the isolated stromal cells at least one of the steps of culturing the cells in vitro, introducing isolated nucleic acid into the cells, and pre-differentiating the cells, is performed.

The invention also includes administering adipose tissue derived stromal cells into the patient in the absence of an immunosuppressive agent.

The present invention includes an isolated adipose tissue derived stromal cell that has been differentiated to express at least one characteristic of a neuronal cell, an astroglial cell, a hematopoietic progenitor cell, or a hepatic cell. In one aspect, the stromal cell is differentiated to express at least one protein characteristic of a non-adipose tissue derived cell. In another aspect, the stromal cell is differentiated to exhibit a morphological characteristic of a non-adipose tissue derived cell.

These cells can be used therapeutically to autologously or allogeneically treat a host in need thereof, or for diagnostic purposes. The cells can be administered, for example, in any pharmaceutically acceptable carrier, including phosphate buffered saline, to the target area. Alternatively, the cells can be administered in a matrix, lattice, or other materials lending two or three dimensional structures to form a structured depot, for example, an implant or a graft. The three dimensional framework can be biodegradable or nonbiodegradable. Examples of biodegradable materials for use in administering these cells include alginate, polylactic acid, polyglycolic acid, polylactide-co-glycolide, proteins such as proteoglycans, glycoproteins, hyaluronins, fibronectins, and collagens. The cells can be administered, if desired, in combination with another agent such as a cytokine, growth factor, chemical inducing agent, biologic, chemotherapeutic, hormone, other cell, protein, carbohydrate, peptide, or nucleic acid.

In a preferred aspect of the invention, stromal cells are derived from subcutaneous, mammary, gonadal, or omental adipose tissues and de-differentiated into fully functional pleuripotent stem cells capable of being partially or completely differentiated into hematopoietic or blood cell lineages, neuronal (nervous system) lineages, astroglial cells, hepatic cells or epithelial lineages. The invention also provides methods of using the induced adipose tissue derived cells therapeutically (for example, in tissue repair, regeneration, reconstruction or enhancement, diagnostically), as bioreactors to produce desired substances, and in genetic and tissue engineering.

The invention provides methods and compositions for the isolation, characterization, and differentiation of adult human extramedullary adipose tissue-derived stromal stem cells along non-mesenchymal lineages, including but not limited to, hematopoietic cells and neuronal cells, and outlines their use as pleuripotent stem cells for the treatment of a number of human and animal conditions and diseases.

In another aspect of the invention, a method for differentiating adipose-tissue derived stromal cells to express at least one characteristic of a non-adipose tissue derived cell, for example, a neuronal, astroglial, hematopoietic progenitor, or hepatic cell, is provided comprising: culturing isolated adipose tissue-derived stromal cells in a chemically defined culture medium that optionally contains serum and appropriate growth factors, hormones, cytokines, serum factors, embryonic extracts, preferably a non-human embryonic extract; and/or chemical compounds to induce specific lineage differentiation. In one aspect, the stromal cell is differentiated to express at least one protein characteristic of a non-adipose tissue derived cell. In another aspect, the stromal cell is differentiated to exhibit a morphological characteristic of a non-adipose tissue derived cell.

In addition, the cells of the present invention can be genetically modified to express a therapeutic gene product. The adipose-derived cells can be genetically modified, e.g., to express exogenous genes or to repress the expression of endogenous genes. In accordance with this embodiment, the cell is exposed to a gene transfer vector comprising a nucleic acid including a transgene, such that the nucleic acid is introduced into the cell under conditions appropriate for the transgene to be expressed within the cell. The transgene generally is an expression cassette, including a coding polynucleotide operably linked to a suitable promoter. The coding polynucleotide can encode a protein, or it can encode biologically active RNA, such as antisene RNA or a ribozyme.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising FIGS. 1A and 1B depict control-BMSC and AP-BMSC, respectively. FIGS. 1C and 1D depict control adipose tissue derived stromal cells and AP-adipose tissue derived stromal cells, respectively.

FIG. 2, comprising FIG. 2A depicts the results of the adhesive-removal patch test. FIG. 2B depicts the results of the modified neurological severity score (mNSS). FIG. 2C depicts the results of the corner test.

DETAILED DESCRIPTION OF THE INVENTION

Figure 1A:
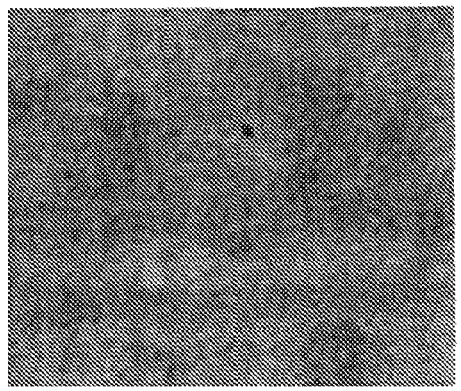
FIG. 1A through FIG. 1D, is a series of images depicting expression of alkaline phosphatase (AP) by BMSCs and adipose tissue derived stromal cells isolated from AP-transgenic rats.
Figure 1B:
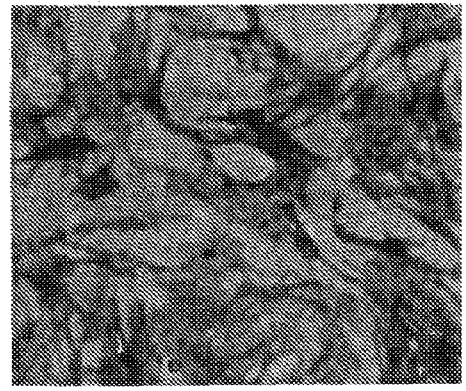
Figure 1C:
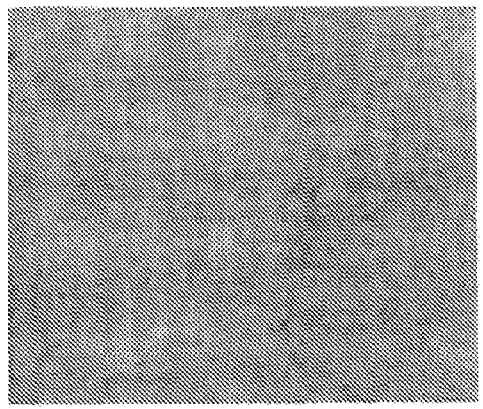
Figure 1D:

The invention provides methods and compositions for adipose tissue-derived stromal cells differentiated to express at least one characteristic of a non-adipose tissue derived cell, preferably a neuronal, astroglial, hepatic or hematopoietic progenitor cell. In one aspect, the stromal cells are differentiated to express at least one protein characteristic of a non-adipose tissue derived cell. In another aspect, the stromal cells are differentiated to exhibit a morphological characteristic of a non-adipose tissue derived cell.

The cells produced by the methods of invention can provide a source of partially or fully differentiated, functional cells having characteristics from multiple tissue lineages for research, transplantation, and development of tissue engineering products for the treatment of animal disease, preferably human disease, and tissue repair or improvement.

Adipose tissue offers a potential alternative to bone marrow as a source of multipotential stromal stem cells. Adipose tissue is readily accessible and abundant in many individuals. Obesity is a condition of epidemic proportions in the United States, where over 50% of adults exceed the recommended body mass index (BMI) based on their height and weight. Adipocytes can be harvested by liposuction on an outpatient basis. Liposuction is a relatively non-invasive procedure with cosmetic effects, which are acceptable to the vast majority of patients. It is well documented that adipocytes are a replenishable cell population. Even after surgical removal by liposuction or other procedures, it is common to see a recurrence of adipocytes in an individual over time at the same site. This suggests that adipose tissue contain cells that are capable of producing new adipose cells.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

As used herein, the term "autologous" is meant to refer to any material derived from the same individual to which it is later to be re-introduced.

As used herein, the term "allogeneic" is meant to refer to any material derived from a different mammal of the same species.

"Xenogeneic" refers to any material derived from a mammal of a different species.

As used herein, the term "phenotypic characteristics" should be construed to mean at least one of the following characteristics: morphological appearance, the expression of a specific protein, a staining pattern, and the ability to be stained with a substance.

As used herein, "central nervous system" should be construed to include brain and/or the spinal cord of a mammal. The term may also include the eye and optic nerve in some instances.

"Differentiation medium" is used herein to refer to a cell growth medium comprising an additive or a lack of an additive such that a stem cell, adipose tissue derived stromal cell, embryonic stem cell, ES-like cell, MSCs, neurosphere, NSC or other such progenitor cell, that is not fully differentiated when incubated in the medium, develops into a cell with some or all of the characteristics of a differentiated cell.

As used herein, the term "disease, disorder or condition of the central nervous system" is meant to refer to a disease, disorder or a condition which is caused by a genetic mutation in a gene that is expressed by cells of the central nervous system such that one of the effects of such a mutation is manifested by abnormal structure and/or function of the central nervous system, such as, for example, neurodegenerative disease or primary tumor formation. Such genetic defects may be the result of a mutated, non-functional or under-expressed gene in a cell of the central nervous system. The term should also be construed to encompass other pathologies in the central nervous system which are not the result of a genetic defect per se in cells of the central nervous system, but rather are the result of infiltration of the central nervous system by cells which do not originate in the central nervous system, for example, metastatic tumor formation in the central nervous system. The term should also be construed to include trauma to the central nervous system induced by direct injury to the tissues of the central nervous system. For example, the term disease, disorder or condition of the central nervous system also can include stroke.

As used herein, "stroke" refers to a disease, disorder or condition of the central nervous system when blood flow to a region of the brain is obstructed and may result in death of brain tissue. There are two main types of stroke: ischemic and hemorrhagic. Ischemic stroke is caused by blockage in an artery that supplies blood to the brain, resulting in a deficiency in blood flow (ischemia). Hemorrhagic stroke is caused by the bleeding of ruptured blood vessels (hemorrhage) in the brain.

"Neural stem cell" or "NSC" is used herein to refer to undifferentiated, multipotent, self-renewing neural cell. A neural stem cell is a clonogenic multipotent stem cell which is able to divide and, under appropriate conditions, has self-renewal capability and can terminally differentiate into among others, neurons, astrocytes, and oligodendrocytes. Hence, the neural stem cell is "multipotent" because stem cell progeny have multiple differentiation pathways. A neural stem cell is capable of self maintenance, meaning that with each cell division, one daughter cell will also be, on average, a stem cell.

As used herein, "central nervous system" should be construed to include brain and/or the spinal cord of a mammal. The term may also include the eye and optic nerve in some instances.

As used herein "endogenous" refers to any material from or produced inside an organism, cell or system.

"Exogenous" refers to any material introduced from or produced outside an organism, cell, or system.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered. Also, as used herein, a "therapeutically effective amount" is the amount of cells which is sufficient to provide a beneficial effect to the subject to which the cells are administered.

Description

In one embodiment of the invention, an adipose tissue derived stromal cell induced to express at least one phenotypic characteristic of a neuronal, astroglial, hepatic or hematopoietic progenitor cell is provided. Phenotypic markers of the desired cells are well known to those of ordinary skill in the art, and copiously published in the literature. Additional phenotypic markers continue to be disclosed or can be identified without undue experimentation. Any of these markers can be used to confirm that the adipose cell has been induced to a differentiated state. Lineage specific phenotypic characteristics can include cell surface proteins, cytoskeletal proteins, cell morphology, and secretory products. Neuronal characteristics include the expression of neuronal markers such as NeuN, NF-M, NSE, nestin, and trkA. Blood specific markers can include the presence of CD4, CD8, CD7, CD19, CD45, CD33, CD34, TCR, etc. One of ordinary skill in the art will recognize that known colorimetric, fluorescent, immunochemical, polymerase chain reaction, chemical or radiochemical methods can readily ascertain the presence or absence of a lineage specific marker.

In another embodiment, the invention provides a dedifferentiated, isolated, adipose tissue derived stromal cell capable of being differentiated to express at least one characteristic of a non-adipose tissue derived cell, for example, neuronal, astroglial, hepatic or hematopoietic progenitor cell. Preferably, the dedifferentiated cell is an uncommitted progenitor cell. In one aspect, the stromal cell is differentiated to express at least one protein characteristic of a non-adipose tissue derived cell. In another aspect, the stromal cell is differentiated to exhibit a morphological characteristic of a non-adipose tissue derived cell. A dedifferentiated adipose derived stromal cell can be identified by the absence of adipocyte markers. In another embodiment the dedifferentiated adipocyte can be provided in combination with a pharmaceutically acceptable carrier for a therapeutic application, including but not limited to tissue repair, regeneration, reconstruction or enhancement. Adipose tissue derived stromal cells can be cultured by the methods disclosed herein to dedifferentiate the stromal cells such that the dedifferentiated stromal cells can then be induced to express characteristics of cells other than adipose tissue derived cells. The dedifferentiated adipocyte can be modified to include a non-endogenous gene sequence for production of a desired protein or peptide. The dedifferentiated adipocyte can, in an alternative embodiment, be administered to a host in a two or three dimensional framework for a desired therapeutic purpose.

In another embodiment of the invention, a method is provided for differentiating adipose tissue-derived stromal cells into cells having the properties of hematopoietic stem cells, neuronal cells, astroglial, hepatic or other lineages, comprising: plating isolated adipose tissue-derived stromal cells at a desired density, including but not limited to a density of about 1,000 to about 500,000 cells/cm$^2$; incubating the cells in a chemically defined culture medium comprising at least one compound selected from the group consisting of: growth factor, hormone, cytokine and serum factor; and optionally, an embryonic extract, preferably a non-human embryonic extract. In another embodiment, the cell is differentiated in the absence of serum but in the presence of a chemical agent, for example, an oxidizing agent such as 2-mercaptoethanol.

In another embodiment, the invention provides a method for differentiating an isolated adipose tissue-derived stromal cell to express at least one characteristic of a cell of non-mesenchymal lineage, comprising: plating isolated adipose tissue-derived stromal cell to a useful density, including but not limited to a density of about 1,000 to about 500,000 cells/cm$^2$; incubating the cells in a chemically defined culture medium at least one compound selected from the group consisting of: growth factors, hormones, cytokines and serum factors; and optionally, an embryonic extract, preferably a non-human embryonic extract. In one aspect, the stromal cell is differentiated to express at least one protein characteristic of a non-adipose tissue derived cell. In another aspect, the stromal cell is differentiated to exhibit a morphological characteristic of a non-adipose tissue derived cell.

In still another embodiment, the invention provides adipose-derived dedifferentiated cells, pleuripotent stem cells and differentiated cells of nonmesenchymal lineages that are produced according to the methods of the invention. Such cells are useful in autologous and allogenic transplantations.

In one preferred embodiment, the site is central nervous system tissue and the desired characteristic or phenotype is neuronal. In a second preferred embodiment, the site is central nervous system tissue and the desired characteristic or phenotype is astroglial. In another preferred embodiment, the site is intravenous and the desired characteristic or cell type is hematopoietic. In yet another embodiment, the site is the hepatic system, and in particular, the liver, and the desired characteristic or phenotype is hepatic. Preferably, the subject is mammalian, more preferably the subject is human.

In yet another embodiment, the invention provides a method of improving hematopoiesis in a patient, comprising transplantation of the cells of the invention into the patient. Preferably, the transplantation is by intravenous infusion. In one embodiment, the cell is transiently or stably transfected with at least one nucleic acid sequence. A viral or other vehicle containing at least one desired nucleic acid sequence to be introduced into the cell may mediate transfection.

The adipose tissue derive stromal cells useful in the methods of invention may be isolated by a variety of methods known to those skilled in the art. For example, such methods are described in U.S. Pat. No. 6,153,432 incorporated herein in its entirety. In a preferred method, adipose tissue is isolated from a mammalian subject, preferably a human subject. A preferred source of adipose tissue is omental adipose. In humans, the adipose is typically isolated by liposuction. If the cells of the invention are to be transplanted into a human subject, it is preferable that the adipose tissue be isolated from that same subject so as to provide for an autologous transplant. Alternatively, the administered tissue may be allogenic.

In one method of isolating adipose tissue derived stromal cells, the adipose tissue is treated with collagenase at concentrations between 0.01 to 0.5%, preferably 0.04 to 0.2%, most preferably about 0.1%, trypsin at concentrations between 0.01 to 0.5%, preferably 0.04%, most preferably about 0.2%; and/or dispase at concentrations of 0.5 ng/ml to 10 ng/ml; and/or effective concentrations of hyaluronidase or DNase; and ethylenediaminetetra-acetic acid (EDTA) at concentrations of about 0.01 to 2.0 mM, preferably at about 0.1 to about 1.0 mM, most preferably at 0.53 mM; at temperatures between 25° to 50° C., preferably between 33° to 40° C., most preferably at 37° C., for periods of between 10 minutes to 3 hours, preferably between 30 minutes to 1 hour, most preferably 45 minutes. The cells are passed through a nylon or cheesecloth mesh filter of between 20 microns to 800 microns, more preferably between 40 to 400 microns, most preferably 70 microns. The cells are then subjected to differential centrifugation directly in media or over a Ficoll or Percoll or other particulate gradient. Cells will be centrifuged at speeds of between 100 to 3000×g, more preferably 200 to 1500×g, most preferably at 500×g for periods of between 1 minutes to 1 hour, more preferably 2 to 15 minutes, most preferably 5 minutes, at temperatures of between 4° to 50° C., preferably between 20° to 40° C., most preferably at about 25° C.

Following isolation, adipose tissue derived stromal cells are incubated in stromal cell medium in a culture apparatus for a period of time or until the cells reach confluency before passing the cells to another culture apparatus. The culturing apparatus can be of any culture apparatus commonly used in culturing cells in vitro. Preferably, the level of confluence is greater than 70% before passing the cells to another culture apparatus. More preferably, the level of confluence is greater than 90%. A period of time can be any time suitable for the culture of cells in vitro. Stromal cell medium may be replaced during the culture of the adipose tissue derived stromal cells at any time. Preferably, the stromal cell medium is replaced every 3 to 4 days. Adipose tissue derived stromal cells are then harvested from the culture apparatus whereupon the adipose tissue derived stromal cells can be used immediately or cryopreserved to be stored for use at a later time. Adipose tissue derived stromal cells may be harvested by trypsinization, EDTA treatment, or any other procedure used to harvest cells from a culture apparatus.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time. Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

The invention comprises the treatment of the adipose tissue derived stromal cells to induce them to form hematopoietic, neuronal, astroglial, hepatic or other lineages of cells. While the invention is not bound by any theory of operation, it is believed that treatment of the preadipocytes with a medium containing a combination of serum, embryonic extracts, preferably a non-human embryonic extract, purified or recombinant growth factors, cytokines, hormones, and/or chemical agents, in a 2-dimensional or 3-dimensional microenvironment, will induce differentiation.

Non-limiting examples of base media useful in the methods of the invention include Minimum Essential Medium Eagle, ADC-1, LPM (Bovine Serum Albumin-free), F10 (HAM), F12 (HAM), DCCM1, DCCM2, RPMI 1640, BGJ Medium (with and without Fitton-Jackson Modification), Basal Medium Eagle (BME—with the addition of Earle's salt base), Dulbecco's Modified Eagle Medium (DMEM—without serum), Yamane, IMEM-20, Glasgow Modification Eagle Medium (GMEM), Leibovitz L-15 Medium, McCoy's 5A Medium, Medium M199 (M199E—with Earle's sale base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with non essential amino acids), among numerous others, including medium 199, CMRL 1415, CMRL 1969, CMRL 1066, NCTC 135, MB 75261, MAB 8713, DM 145, Williams' G, Neuman & Tytell, Higuchi, MCDB 301, MCDB 202, MCDB 501, MCDB 401, MCDB 411, MDBC 153. A preferred medium for use in the present invention is DMEM. These and other useful media are available from GIBCO, Grand Island, N.Y., USA and Biological Industries, Bet HaEmek, Israel, among others. A number of these media are summarized in Methods in Enzymology, Volume LVIII, "Cell Culture", pp. 62-72, edited by William B. Jakoby and Ira H. Pastan, published by Academic Press, Inc.

Additional non-limiting examples of media useful in the methods of the invention can contain fetal serum of bovine or other species at a concentration of at least 1% to about 30%, preferably at least about 5% to 15%, mostly preferably about 10%. Embryonic extract of chicken or other species can be present at a concentration of about 1% to 30%, preferably at least about 5% to 15%, most preferably about 10%.

By "growth factors, cytokines, hormones" is intended the following specific factors including, but not limited to, growth hormone, erythropoeitin, thrombopoietin, interleukin 3, interleukin 6, interleukin 7, macrophage colony stimulating factor, c-kit ligand/stem cell factor, osteoprotegerin ligand, insulin, insulin like growth factors, epidermal growth factor, fibroblast growth factor, nerve growth factor, cilary neurotrophic factor, platelet derived growth factor, and bone morphogenetic protein at concentrations of between picogram/ml to milligram/ml levels. At such concentrations, the growth factors, cytokines and hormones useful in the methods of the invention are able to induce, up to 100% the formation of blood cells (lymphoid, erythroid, myeloid or platelet lineages) from adipose derived stromal cells in colony forming unit (CFU) assays. (Moore et al., 1973, J. Natl. Cancer Inst. 50:603-623; Lee et al., 1989, J. Immunol. 142:3875-3883; Medina et al., 1993, J. Exp. Med. 178:1507-1515).

It is further recognized that additional components may be added to the culture medium. Such components may be antibiotics, antimycotics, albumin, amino acids, and other components known to the art for the culture of cells. Additionally, components may be added to enhance the differentiation process.

By "chemical agents" is meant to include, but not be limited to, antioxidant compounds such as butylated hydroxyanisole (BHA) or 2-mercaptoethanol, steroids, retinoids, and other chemical compounds or agents that induce the differentiation of adipose derived stromal cells.

By "characterization" of the resulting differentiated cells is intended the identification of surface and intracellular proteins, genes, and/or other markers indicative of the lineage commitment of the stromal cells to a particular terminal differentiated state. These methods will include, but are not limited to, (a) detection of cell surface proteins by immunofluorescent methods using protein specific monoclonal antibodies linked using a secondary fluorescent tag, including the use of flow cytometric methods; (b) detection of intracellular proteins by immunofluorescent methods using protein specific monoclonal antibodies linked using a secondary fluorescent tag, including the use of flow cytometric methods; (c) detection of cell genes by polymerase chain reaction, in situ hybridization, and/or northern blot analysis.

Partially or terminally differentiated cells may be characterized by the identification of surface and intracellular proteins, genes, and/or other markers indicative of the lineage commitment of the stromal cells to a particular terminal differentiated state. These methods will include, but are not limited to, (a) detection of cell surface proteins by immunofluorescent assays such as flow cytometry or in situ immunostaining of adipose-derived stromal cells surface proteins such as alkaline phosphatase, CD44, CD146, integrin beta 1 or osteopontin (Gronthos et al., 1994, Blood 84:4164-4173); (b) detection of intracellular proteins by immunofluorescent methods such as flow cytometry or in situ immunostaining of adipose tissue-derived stromal cells using specific monoclonal antibodies directed against peroxisome proliferator activated receptors, retinoid X receptors, vitamin D receptors or Cbfal; (c) detection of the expression of lineage selective mRNAs such as osteocalcin, PPAR gamma, leptin, Cbfal, interleukin 7, osteoprotegerin ligand and/or macrophage colony stimulating factor, leukocyte marker and growth factor by methods such as polymerase chain reaction, in situ hybridization, and/or other blot analysis (See Gimble et al., 1989, Blood 74:303-311).

The cells may be administered into a host in order in a wide variety of ways. Preferred modes of administration are parenteral, intraperitoneal, intravenous, intradermal, epidural, intraspinal, intrasternal, intra-articular, intra-synovial, intrathecal, intra-arterial, intracardiac, intramuscular, intranasal, subcutaneous, intraorbital, intracapsular, topical, transdermal patch, via rectal, vaginal or urethral administration including via suppository, percutaneous, nasal spray, surgical implant, internal surgical paint, infusion pump, or via catheter. In one embodiment, the agent and carrier are administered in a slow release formulation such as a direct tissue injection or bolus, implant, microparticle, microsphere, nanoparticle or nanosphere.

The presence of the differentiated cells of the invention may be detected in a subject by a variety of techniques including, but not limited to, flow cytometric, immunohistochemical, in situ hybridization, and/or other histologic or cellular biologic techniques. See, for example, Kopen et al., 1999, Proc Natl Acad Sci 96:10711-10716.

Disorders that can be treated by infusion of the disclosed cells include, but are not limited to, diseases resulting from a failure of a dysfunction of normal blood cell production and maturation (i.e., aplastic anemia and hypoproliferative stem cell disorders); neoplastic, malignant diseases in the hematopoietic organs (e.g., leukemia and lymphomas); broad spectrum malignant solid tumors of non-hematopoietic origin; autoimmune conditions; and genetic disorders. Such disorders include, but are not limited to diseases resulting from a failure or dysfunction of normal blood cell production and maturation hyperproliferative stem cell disorders, including aplastic anemia, pancytopenia, agranulocytosis, thrombocytopenia, red cell aplasia, Blackfan-Diamond syndrome, due to drugs, radiation, or infection, idiopathic; hematopoietic malignancies including acute lymphoblastic (lymphocytic) leukemia, chronic lymphocytic leukemia, acute myelogenous leukemia, chronic myelogenous leukemia, acute malignant myelosclerosis, multiple myeloma, polycythemia vera, agnogenic myelometaplasia, Waldenstrom's macroglobulinemia, Hodgkin's lymphoma, non-Hodgkin's lymphoma; immunosuppression in patients with malignant, solid tumors including malignant melanoma, carcinoma of the stomach, ovarian carcinoma, breast carcinoma, small cell lung carcinoma, retinoblastoma, testicular carcinoma, glioblastoma, rhabdomyosarcoma, neuroblastoma, Ewing's sarcoma, lymphoma; autoimmune diseases including rheumatoid arthritis, diabetes type I, chronic hepatitis, multiple sclerosis, systemic lupus erythematosus; genetic (congenital) disorders including anemias, familial aplastic, Fanconi's syndrome, dihydrofolate reductase deficiencies, formamino transferase deficiency, Lesch-Nyhan syndrome, congenital dyserythropoietic syndrome I-IV, Chwachmann-Diamond syndrome, dihydrofolate reductase deficiencies, formamino transferase deficiency, Lesch-Nyhan syndrome, congenital spherocytosis, congenital elliptocytosis, congenital stomatocytosis, congenital Rh null disease, paroxysmal nocturnal hemoglobinuria, G6PD (glucose-6-phosphate dehydrogenase) variants 1, 2, 3, pyruvate kinase deficiency, congenital erythropoietin sensitivity, deficiency, sickle cell disease and trait, thalassemia alpha, beta, gamma, met-hemoglobinemia, congenital disorders of immunity, severe combined immunodeficiency disease (SCID), bare lymphocyte syndrome, ionophore-responsive combined immunodeficiency, combined immunodeficiency with a capping abnormality, nucleoside phosphorylase deficiency, granulocyte actin deficiency, infantile agranulocytosis, Gaucher's disease, adenosine deaminase deficiency, Kostmann's syndrome, reticular dysgenesis, congenital Leukocyte dysfunction syndromes; and others such as osteoporosis, myelosclerosis, acquired hemolytic anemias, acquired immunodeficiencies, infectious disorders causing primary or secondary immunodeficiencies, bacterial infections (e.g., Brucellosis, Listerosis, tuberculosis, leprosy), parasitic infections (e.g., malaria, Leishmaniasis), fungal infections, disorders involving disproportionsin lymphoid cell sets and impaired immune functions due to aging, phagocyte disorders, Kostmann's agranulocytosis, chronic granulomatous disease, Chediak-Higachi syndrome, neutrophil actin deficiency, neutrophil membrane GP-180 deficiency, metabolic storage diseases, mucopolysaccharidoses, mucolipidoses, miscellaneous disorders involving immune mechanisms, Wiskott-Aldrich Syndrome, alpha 1-antirypsin deficiency, etc.

Diseases or pathologies include neurodegenerative diseases, hepatodegenerative diseases, nephrodegenerative disease, spinal cord injury, head trauma or surgery, viral infections that result in tissue, organ, or gland degeneration, and the like. Such neurodegenerative diseases include but are not limited to, AIDS dementia complex; demyeliriating diseases, such as multiple sclerosis and acute transferase myelitis; extrapyramidal and cerebellar disorders, such as lesions of the ecorticospinal system; disorders of the basal ganglia or cerebellar disorders; hyperkinetic movement disorders, such as Huntington's Chorea and senile chorea; drug-induced movement disorders, such as those induced by drugs that block CNS dopamine receptors; hypokinetic movement disorders, such as Parkinson's disease; progressive supra-nucleo palsy; structural lesions of the cerebellum; spinocerebellar degenerations, such as spinal ataxia, Friedreich's ataxia, cerebellar cortical degenerations, multiple systems degenerations (Mencel, Dejerine Thomas, Shi-Drager, and Machado-Joseph), systemic disorders, such as Rufsum's disease, abetalipoprotemia, ataxia, telangiectasia; and mitochondrial multi-system disorder; demyelinating core disorders, such as multiple sclerosis, acute transverse myelitis; and disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Demetia of Lewy body type; Wernicke-Korsakoff syndrome; chronic alcoholism; Creutzfeldt-Jakob disease; Subacute sclerosing panencephalitis hallerrorden-Spatz disease; and Dementia pugilistica. See, e.g., Berkow et. al., (eds.) (1987), The Merck Manual, ($15^{th}$) ed.), Merck and Co., Rahway, N.J., which reference, and references cited therein, are entirely incorporated herein by reference.

In another embodiment, the adipose-derived cells can be genetically modified, e.g., to express exogenous genes or to repress the expression of endogenous genes. In accordance with this embodiment, the cell is exposed to a gene transfer vector comprising a nucleic acid including a transgene, such that the nucleic acid is introduced into the cell under conditions appropriate for the transgene to be expressed within the cell. The transgene generally is an expression cassette, including a coding polynucleotide operably linked to a suitable promoter. The coding polynucleotide can encode a protein, or it can encode biologically active RNA, such as antisene RNA or a ribozyme. Thus, the coding polynucleotide can encode a gene conferring, for example, resistance to a toxin, a hormone (such as peptide growth hormones, hormone releasing factor, sex hormones, adrenocorticotrophic hormones, cytokines such as interferons, interleukins, and lymphokines), a cell surface-bound intracellular signaling moiety such as cell-adhesion molecules and hormone receptors, and factors promoting a given lineage of differentiation, or any other transgene with known sequence.

The expression cassette containing the transgene should be incorporated into the genetic vector suitable for delivering the transgene to the cell. Depending on the desired end application, any such vector can be so employed to genetically modify the cells (e.g., plasmids, naked DNA, viruses such as adenovirus, adeno-associated virus, herpesvirus, lentivirus, papillomavirus, retroviruses, etc.). Any method of constructing the desired expression cassette within such vectors can be employed, many of which are well known in the art, such as by direct cloning, homologous recombination, etc. The desired vector will largely determine the method used to introduce the vector into the cells, which are generally known in the art. Suitable techniques include protoplast fusion, calcium-phosphate precipitation, gene gun, electroporation, and infection with viral vectors.

The cells described herein can be used in combination with any known technique of tissue engineering, including but not limited to those technologies described in patents and publications cited in the Background of the Invention (including U.S. Pat. Nos. 5,902,741 and 5,863,531 to Advanced Tissue Sciences, Inc.) as well as, but not limited to: U.S. Pat. No. 6,139,574, Vacanti et al. (Oct. 31, 2000) Vascularized Tissue Regeneration Matrices Formed By Solid Free Form Fabrication Techniques; U.S. Pat. No. 5,759,830, Vacanti et al. (Jun. 2, 1998) Three-Dimensional Fibrous Scaffold Containing Attached Cells For Producing Vascularized Tissue In Vivo; U.S. Pat. No. 5,741,685, Vacanti, (Apr. 21, 1998) Parenchymal Cells Packaged In Immunoprotective Tissue For Implantation; U.S. Pat. No. 5,736,372, Vacanti et al. (Apr. 7, 1998) Biodegradable Synthetic Polymeric Fibrous Matrix Containing Chondrocyte For In Vivo Production Of A Cartilaginous Structure; U.S. Pat. No. 5,804,178, Vacanti et al. (Sep. 8, 1998) Implantation Of Cell-Matrix Structure Adjacent Mesentery, Omentum Or Peritoneum Tissue; U.S. Pat. No. 5,770,417, Vacanti et al. (Jun. 23, 1998) Three-Dimensional Fibrous Scaffold Containing Attached Cells For Producing Vascularized Tissue In Vivo; U.S. Pat. No. 5,770,193, Vacanti et al. (Jun. 23, 1998) Preparation of Three-Dimensional Fibrous Scaffold For Attaching Cells To Produce Vascularized Tissue In Vivo; U.S. Pat. No. 5,709,854, Griffith-Cima et al. (Jan. 20, 1998) Tissue Formation By Injecting A Cell-Polymeric Solution That Gels In Vivo; U.S. Pat. No. 5,516, 532, Atala et al. (May 14, 1998) Injectable Non-Immunogenic Cartilage And Bone Preparation; U.S. Pat. No. 5,855, 610, Vacanti et al. (Jan. 5, 1999) Engineering Of Strong, Pliable Tissues; U.S. Pat. No. 5,041,138, Vacanti et al. (Aug. 20, 1991) Neomorphogenesis Of Cartilage In Vivo From Cell Culture; U.S. Pat. No. 6,027,744, Vacanti et al. (Feb. 22, 1900) Guided Development and Support Of Hydrogel-Cell Compositions; U.S. Pat. No. 6,123,727, Vacanti et al. (Sep. 26, 2000) Tissue Engineered Tendons And Ligament; U.S. Pat. No. 5,536,656, Kemp et al. (Jul. 16, 1996) Preparation Of Tissue Equivalents By Contraction Of A Collagen Gel Layered On A Collagen Gel; U.S. Pat. No. 5,144,016, Skjak-Braek et al. (Sep. 1, 1992) Alginate Gels; U.S. Pat. No. 5,944,754, Vacanti (Aug. 31, 1999) Tissue Re-Surfacing With Hydrogel-Cell Compositions; U.S. Pat. No. 5,723,331, Tubo et al. (Mar. 3, 1998) Methods And Compositions For The Repair Of Articular Cartilage Defects In Mammals; U.S. Pat. No. 6,143,501, Sittinger et al. (Nov. 7, 2000) Artificial Tissues, Methods For The Production And The Use Thereof.

Therapeutic Methods

The present invention provides a method of treating neural injury and neurodegeneration using adipose tissue derived stromal cells in a mammal, preferably a human. It has been demonstrated that adipose tissue derived stromal cells within injured brain and/or spinal cord produce an array of factors including, but not limited to, cytokines and growth factors. The adipose tissue derived stromal cells activate endogenous stem cells and ependymal cells in the brain, to proliferate and differentiate into parenchymal cells including, but not limited to, neurons. These new neurons can be present at sites adjacent to the sites of injury, for example the dentate gyrus and olfactory bulb. Thus, the adipose tissue derived stromal cells activate endogenous CNS stem cells to differentiate into neurons. The adipose tissue derived stromal cells also produce factors including, but not limited to cytokines and growth factors, that promote repair and plasticity of the brain.

The present invention encompasses methods for administering the cells of the present invention to a mammal. The cells can be transplanted into the penumbral tissue, which is a tissue adjacent to a lesion. The tissue adjacent to the lesion provides a receptive environment, similar to that of a developing brain, for the survival and differentiation of the adipose tissue derived stromal cells.

In addition, adipose tissue derived stromal cells are effective in treating neural injury and degeneration when these cells are administered intravascularly, i.e. intraarterially or intravenously. Therefore, after such brain injury when the brain tissue is damaged, in an effort to compensate for the lost tissue, the administration of adipose tissue derived stromal cells provides a sufficient source of cells to promote compensatory responses of the brain to such damage.

The cells of the present invention can be administered into including, but not limited to ischemic brain, injured brain, injured spinal cord, and into brain that exhibits symptoms of stroke. Administration of the cells into the mammal can also be performed in combination with growth factors including, but not limited to brain derived neurotrophic factor (BDNF) and nerve growth factor (NGF). The cells of the invention can be cultured with nerve growth factor (NGF) prior to administration to the mammal. The cells can also be cultured in any neuronal differentiation medium prior to administration to the mammal.

Administration of adipose tissue derived stromal cells can occur at various time points. For example, the cells can be administered from about 2 hours from the onset of the stroke event. In one aspect, the cells can be administered from about 1 day, preferably 2 days, more preferably 3 days, preferably 4 days, and more preferably 7 days from the onset of the stroke event. In another aspect, the cells can be administered to a mammal weeks after the onset of stroke.

The administration of adipose tissue derived stromal cells into ischemic brain can result in the differentiation of the adipose tissue derived stromal cells into the brain parenchymal cells, including but not limited to neurons. In addition, the adipose tissue derived stromal cells can secrete factors that activate the proliferation and differentiation of endogenous stem cells located in the brain into parenchymal cells. In one aspect of the invention, the secreted factors migrate and target distant cells. In another aspect, the cells of the invention migrate to different regions within the brain including, but not limited to, the hippocampus, the striatum, the olfactory bulb and the cortex, where the cells secrete factors that are beneficial to the neighboring cells in the host brain.

The present invention is based on the discovery that adipose tissue derived stromal cells can differentiate into neurons and other parenchymal cells. In addition, the present invention is based on the discovery that adipose tissue derived stromal cells can secrete a factor that is beneficial to neighboring and/or distant cells. The disclosure presented herein demonstrates that when adipose tissue derived stromal cells are introduced into a mammal, the adipose tissue derived stromal cells activate endogenous cells to proliferate and differentiate into cells of the CNS. The present disclosure also demonstrates that adipose tissue derived stromal cells when introduced to a site, or near a site of brain injury and/or spinal cord injury, produce and secrete an array of factors including, but not limited to trophic factors, cytokines and growth factors. The factors secreted by the adipose tissue derived stromal cells serve to activate endogenous stem cells and/or epedymal cells in the brain and/or spinal cord to proliferate and differentiate into parenchymal cells, including, but not limited to neurons. Thus, the present invention includes a method of using adipose tissue derived stromal cells to promote repair and plasticity of a CNS tissue in a mammal including, but not limited to brain and spinal cord diseases.

The cells of the present invention can also be used to secrete an angiogenic hormone including, but not limited to vascular growth factor, endothelial cell growth factor, and the like. Adipose tissue derived stromal cells can be used to induce angiogenesis within the tissue in which the adipose tissue derived stromal cells are present. Thus, the invention provides a method of promoting neovascularization within a tissue using such cells. In accordance with this method, the cells are introduced to the desired tissue under conditions sufficient for the cell to produce an angiogenic hormone. The presence of the hormone within the tissue promotes neovascularization within the tissue.

The mode of administration of the cells of the invention to the CNS of the mammal may vary depending on several factors including the type of disease being treated, the age of the mammal, whether the cells are differentiated or not, whether the cells have heterologous DNA introduced therein, and the like. An example of administration of the cells into a brain tissue is provided herein in the experimental Examples section. In that example, cells are introduced into the brain of a mammal by intracerebral or intravascular transplantation. Cells may be introduced to the desired site by direct injection, or by any other means used in the art for the introduction of compounds into the CNS.

Transplantation of the cells of the present invention can be accomplished using techniques well known in the art as well as those described herein or as developed in the future. The present invention comprises a method for transplanting, grafting, infusing, or otherwise introducing the cells into a mammal, preferably, a human. Exemplified herein are methods for transplanting the cells into a brain of a mammal, but the present invention is not limited to such anatomical sites. Also, methods for bone transplants are well known in the art and are described in, for example, U.S. Pat. No. 4,678,470, pancreas cell transplants are described in U.S. Pat. No. 6,342, 479, and U.S. Pat. No. 5,571,083, teaches methods for transplanting cells to any anatomical location in the body.

In order to transplant the cells of the present invention into a human, the cells are prepared as described herein. Preferably, the cells are from the patient for which the cells are being transplanted into (autologous transplantation). One preferable mode of administration is as follows. In the case where cells are not from the patient (allogeneic transplantation), at a minimum, blood type or haplotype compatibility should be determined between the donor cell and the patient. Surgery is performed using a Brown-Roberts-Wells computed tomographic (CT) stereotaxic guide. The patient is given local anesthesia in the scalp area and intravenously administered midazolam. The patient undergoes CT scanning to establish the coordinates of the region to receive the transplant. The injection cannula usually consists of a 17-gauge stainless steel outer cannula with a 19-gauge inner stylet. This is inserted into the brain to the correct coordinates, then removed and replaced with a 19-gauge infusion cannula that has been preloaded with about 30 μl of tissue suspension. The cells are slowly infused at a rate of about 3 μl/min as the cannula is withdrawn. Multiple stereotactic needle passes are made throughout the area of interest, approximately 4 mm apart. The patient is examined by CT scan postoperatively for hemorrhage or edema. Neurological evaluations are performed at various post-operative intervals, as well as PET scans to determine metabolic activity of the implanted cells.

Between about $10^5$ and about $10^{13}$ cells per 100 kg person are administered to a human. In some embodiments, between about $1.5\times10^6$ and about $1.5\times10^{12}$ cells are administered per 100 kg person. In some embodiments, between about $1\times10^9$ and about $5\times10^{11}$ cells are administered per 100 kg person. In some embodiments, between about $4\times10^9$ and about $2\times10^{11}$ cells are administered per 100 kg person. In other embodiments, between about $5\times10^8$ cells and about $1\times10^{10}$ cells are administered per 100 kg person. The cells can be administered to a person by various methods including but not limited to infusion and intravenous administration.

In some embodiments, a single administration of cells is provided. In some embodiments, multiple administrations are provided. In some embodiments, multiple administrations are provided over the course of 3-7 consecutive days. In some embodiments, 3-7 administrations are provided over the course of 3-7 consecutive days. In other embodiments, 5 administrations are provided over the course of 5 consecutive days.

In some embodiments, a single administration of between about $10^5$ and about $10^{13}$ cells per 100 kg person is provided. In some embodiments, a single administration of between about $1.5\times10^8$ and about $1.5\times10^{12}$ cells per 100 kg person is provided. In some embodiments, a single administration of between about $1\times10^9$ and about $5\times10^{11}$ cells per 100 kg person is provided. In some embodiments, a single administration of about $5\times10^{10}$ cells per 100 kg person is provided. In some embodiments, a single administration of $1\times10^{10}$ cells per 100 kg person is provided.

In some embodiments, multiple administrations of between about $10^5$ and about $10^{13}$ cells per 100 kg person are provided. In some embodiments, multiple administrations of between about $1.5\times10^8$ and about $1.5\times10^{12}$ cells per 100 kg person are provided. In some embodiments, multiple administrations of between about $1\times10^9$ and about $5\times10^{11}$ cells per 100 kg person are provided over the course of 3-7 consecutive days. In some embodiments, multiple administrations of about $4\times10^9$ cells per 100 kg person are provided over the course of 3-7 consecutive days. In some embodiments, multiple administrations of about $2\times10^{11}$ cells per 100 kg person are provided over the course of 3-7 consecutive days. In some embodiments, 5 administrations of about $3.5\times10^9$ cells are provided over the course of 5 consecutive days. In some embodiments, 5 administrations of about $4\times10^9$ cells are provided over the course of 5 consecutive days. In some embodiments, 5 administrations of about $1.3\times10^{11}$ cells are provided over the course of 5 consecutive days. In some embodiments, 5 administrations of about $2\times10^{11}$ cells are provided over the course of 5 consecutive days.

In one embodiment of the invention, the cells of the present invention are administered to a mammal suffering from a disease, disorder or condition involving the CNS, in order to augment or replace the diseased and damaged cells of the CNS. Adipose tissue derived stromal cells are preferably administered to a human suffering from a disease, disorder or condition involving the CNS. The adipose tissue derived stromal cells are further preferably administered to the brain or spinal cord of the human. In some instances, the cells are administered to the adjacent site of injury in the human brain. The precise site of administration of the cells depends on any number of factors, including but not limited to, the site of the lesion to be treated, the type of disease being treated, the age of the human and the severity of the disease, and the like. Determination of the site of administration is well within the skill of the artisan versed in the administration of such cells. Based on the present disclosure, the cells can be administered to the patient via intracarotid or intravenous routes.

There are several ways in which adipose tissue derived stromal cells can be used in a mammal, preferably a human, to treat diseases of the central nervous system. For example, the cells can be used as precursor cells that differentiate following introduction into the CNS or as cells which have been differentiated into neural cells prior to introduction into the CNS. In either situation, the cells can be differentiated to express at least one protein characteristic of a cell of the CNS including, but not limited to class III β-tubulin, the M subunit of neurofilaments, tyrosine hydroxylase, gluatmate receptor subunits of the GluR1-4 and GluR6 classes, glial fibrillary acidic protein, myelin basic protein, brain factor 1, NeuN, NF-M, NSE, nestin, and trkA.

The data presented herein establish that adipose tissue derived stromal cells, when transplanted into a mammal, express proteins characteristic of astrocytes (positive for glial fibrillary acidic protein, GFAP, a marker for early astrocytes) and neurons (positive for microtubule associate protein-2, MAP-2, a marker for neurons). It is anticipated that adipose tissue derived stromal cells which are introduced into the CNS can differentiate into other cell types including, but not limited to oligodendrocytes, Schwann cells and parenchymal cells.

Further, the disclosure herein demonstrates that following introduction of adipose tissue derived stromal cells into a mammal, the cells can secrete various factors. Such factors include, but are not limited to, growth factors, trophic factors and cytokines. In some instances, the secreted factors can have a therapeutic effect in the mammal. The secreted factors can activate the cell from which the factor was secreted from. In addition, the secreted factor can activate neighboring and/or distal endogenous cells to proliferate and/or differentiate. Preferably an adipose tissue derived stromal cell secretes a cytokine or growth hormone such as human growth factor, fibroblast growth factor, nerve growth factor, insulin-like growth factors, hematopoietic stem cell growth factors, members of the fibroblast growth factor family, members of the platelet-derived growth factor family, vascular and endothelial cell growth factors, members of the TGFβ family (including bone morphogenic factor), or enzymes specific for congenital disorders.

Adipose tissue derived stromal cells can also secrete factors, trophic factors, and cytokines. Without wishing to be bound by any particular theory, it is believed that adipose tissue derived stromal cells can secrete factors including, but not limited to, leukemia inhibitory factor (LIF), brain-derived neurotrophic factor (BDNF), epidermal growth factor receptor (EGF), basic fibroblast growth factor (bFGF), FGF-6, glial-derived neurotrophic factor (GDNF), granulocyte colony-stimulating factor (GCSF), hepatocyte growth factor (HGF), IFN-γ, insulin-like growth factor binding protein (IG-FBP-2), IGFBP-6, IL-1ra, IL-6, IL-8, monocyte chemotactic protein (MCP-1), mononuclear phagocyte colony-stimulating factor (M-CSF), neurotrophic factors (NT3), tissue inhibitor of metalloproteinases (TIMP-1), TIMP-2, tumor necrosis factor (TNF-β), vascular endothelial growth factor (VEGF), VEGF-D, urokinase plasminogen activator receptor (uPAR), bone morphogenetic protein 4 (BMP4), IL1-a, IL-3, leptin, stem cell factor (SCF), stromal cell-derived factor-1 (SDF-1), platelet derived growth factor-BB (PDGFBB), transforming growth factors beta TGFβ-1 and TGFβ-3.

Based on the present disclosure, it is believed that the cells can migrate to different regions within the brain including, but not limited to hippocampus, olfactory bulb and cortex. These cells may therefore replace cells in the CNS which have been lost as a result of a genetic disease, trauma, or other injury. In some situations, the cells do not replace the damaged cells of the CNS, but rather serve to activate endogenous cells to proliferate and/or differentiate into neurons. In any event, the cells of the present invention serve to stimulate endogenous restoration or neurological function in the injured brain.

In addition, prior to the introduction of the cells into the CNS, the cells may be genetically engineered to produce molecules such as trophic factors, growth factors, cytokines, neurotrophins, and the like, which are beneficial to cells which are already present in the CNS. For example, adipose tissue derived stromal cells can be cultured and genetically engineered prior to their introduction into a recipient, and following the introduction of the engineered cell into the recipient, the cells are able to repair the defected CNS tissue.

Based on these considerations, the types of diseases which are treatable using the cells of the present are numerous. For example, among neonates and children, the cells may be used for treatment of a number of genetic diseases of the CNS, including, but not limited to, Tay-Sachs disease and the related Sandhoffs disease, Hurler's syndrome and related mucopolysaccharidoses and Krabbe's disease. To varying extents, these diseases also produce lesions in the spinal cord and peripheral nerves. In addition, in neonates and children, treatment of head trauma during birth or following birth is treatable by introducing the cells into the CNS of the individual. CNS tumor formation in children is also treatable using the methods of the present invention.

With respect to adult diseases of the CNS, the cells of the present invention are useful for treatment of Parkinson's disease, Alzheimer's disease, spinal cord injury, stroke, trauma, tumors, degenerative diseases of the spinal cord such as amyotropic lateral sclerosis, Huntington's disease, epilepsy and the like. Treatment of multiple sclerosis is also possible.

In some aspects of the invention, an individual suffering from a disease, disorder, or a condition that affects the CNS that is characterized by a genetic defect may be treated by supplementing, augmenting and/or replacing defective or deficient neurological cells with cells that correctly express a normal neurological cell gene. The cells which are to be introduced into the individual may be derived from a different donor (allogeneic) or they may be cells obtained from the individual to be treated (autologous). In addition, the cells to be introduced into the individual can be obtained from an entirely different species (xenogeneic). The cells may also be genetically modified to correct the defect. But this is not the only instance where the cells can be genetically modified.

In another aspect of the invention, a mammal suffering from a disease, disorder or a condition of the central nervous system can be treated as follows. Isolated adipose tissue derived stromal cells are obtained and expanded in culture. The cells are then administered to the mammal in need thereof. It is envisioned that some of the isolated/expanded cells that are administered to the mammal develops into cells of the central nervous system. Thus, repopulation of the central nervous system tissue with an expanded population of adipose tissue derived stromal cells serves to provide a population of central nervous system cells which facilitate correction of the defect in the central nervous system tissue. In addition, the cells that are introduced into the mammal can secrete agents including, but not limited to growth factors, trophic factors, cytokines and the like to activate endogenous cells of the mammal to proliferate and differentiate.

It is envisioned that the adipose tissue derived stromal cells of the present invention can be administered to a mammal in need thereof without the requirement of using immunosuppressive drug therapy in addition to the cells. However, such drug therapy, in combination with the cells is also contemplated to be included in the present invention. It is recognized that cells obtained from and administered to disparate mammals runs the risk of graft rejection. It is contemplated that adipose tissue derived stromal cells of the invention do not induce an immune response when the cells are administered to an allogeneic recipient. Further, the presence of an immunosuppressive drug, for example cyclosporine A (CsA) during transplantation of adipose tissue derived stromal cells to an allogeneic mammal will not contribute anymore significant effects on neurological functional recovery compared to when adipose tissue derived stromal cells are administered to an otherwise identical mammal that does not receive the immunosuppressive drug. Therefore, as more fully discussed elsewhere herein, an aspect of the invention includes using allogeneic adipose tissue derived stromal cells for transplantation, preferably, without the concomitant use of an immunosuppressive drug.

The invention also includes methods of using the adipose tissue derived stromal cells of the present invention in conjunction with current modes of treatment, for example, the use of immunosuppressive drug therapy, for the treatment of host rejection to the donor tissue or graft versus host disease. An advantage of using adipose tissue derived stromal cells in conjunction with immunosuppressive drugs in transplantation is that the present invention ameliorates the severity of the severity of the immune response and thus, the amount of immunosuppressive drug therapy used and/or the frequency of administration of immunosuppressive drug therapy can be reduced. A benefit of reducing the use of immunosuppressive drug therapy is the alleviation of general immune suppression and unwanted side effects associated with immunosuppressive drug therapy.

In another aspect of the invention, the cells are pre-differentiated into, for example, neurons prior to administration of the cells into the mammal in need thereof. Adipose tissue derived stromal cells can be differentiated in vitro by treating the cells with differentiation factors including, but are not limited to antioxidants, epidermal growth factor (EGF), and brain derived neurotrophic factor (BDNF). It has been demonstrated that treatment of the cells with these factors induced the cells to undergo morphologic changes consistent with neuronal differentiation, i.e., the extension of long cell processes terminating in growth cones and filopodia. In addition, it was observed that these agents induced the expression of neuronal specific proteins including, but are not limited to nestin, neuron-specific enolase (NSE), neurofilament M (NF-M), neuron-specific nuclear protein (NeuN), and the nerve growth factor receptor trkA.

Treating CNS Disorders

Treating a human patient having a disease, disorder, or a condition that affects the CNS, encompasses among others, intracerebral grafting of adipose tissue derived stromal cells or differentiated adipose tissue derived stromal cells to the CNS, including the region of the CNS having the injury, or a region adjacent to the site of injury. Differentiated adipose tissue derived stromal cells include, for example, oligodendrocyte precursors that have been differentiated by culturing adipose tissue derived stromal cells in a differentiation medium. The cells of the invention can be injected into a number of sites, including the intraventricular region, the parenchyma (either as a blind injection or to a specific site by stereotaxic injections), and the subarachnoid or subpial spaces. Specific sites of injection can be portions of the cortical gray matter, white matter, basal ganglia, and spinal cord. Without wishing to be bound by any particular theory, any mammal affected by a CNS disorder, as described elsewhere herein, can be so treated by one or more of the methodologies described herein.

Conventional techniques for grafting are described, for example, in Bjorklund and Stenevi (1985, Neural Grafting in the Mammalian CNS, eds. Elsevier, pp 169-178), the contents of which are incorporated by reference. Procedures include intraparenchymal transplantation, achieved by injecting the cells of the invention into the host brain tissue. However, transplantation of the cells of the invention can be effected in a number of CNS regions. In addition, the cells can be delivered to the recipient by intravenous administration.

According to the present invention, administration of cells into selected regions of a patient's brain may be made by drilling a hole and piercing the dura to permit the needle of a microsyringe to be inserted. Alternatively, the cells can be injected intrathecally into a spinal cord region. The cell preparation of the invention permits grafting of the cells to any predetermined site in the brain or spinal cord. It also is possible to effect multiple grafting concurrently, at several sites, using the same cell suspension, as well as mixtures of cells.

The invention includes methods of providing a therapeutic effect to a mammal in need thereof. The method includes administering the cells of the present invention to a mammal that has undergone a disease, disorder, or a condition that affects the CNS, otherwise a CNS injury, for example stroke using intraarterial (IA) or intravenous (IV) delivery systems. The effects of adipose tissue derived stromal cells injected via IA or IV in an injured mammal can assessed by analyzing neurological function, neurogenesis, and angiogenesis in mammals that were subjected to ischemic conditions. Quantitative analysis using immunohistochemistry techniques can be performed to assess the level of angiogenesis in the mammal following the administration of the cells of the present invention. Without wishing to be bound by any particular theory, it is believed that there is no significant differences in therapeutic outcome with respect to neurological function, neurogenesis, and angiogenesis in mammals that receive either IA or IV administration of the cells. Adipose tissue derived stromal cells that are delivered to the ischemic brain through both intracarotid and intravenous routes provide therapeutic benefits to a mammal that has undergone stroke. However, the invention should in no way be construed to be limited to any one method of administering adipose tissue derived stromal cells. Rather, any method of administration of the cells should be construed to be included in the present invention. Further, the invention should in no way be limited to stroke, rather, any disease, disorder or condition of the CNS can be treated using compositions and methods of the present invention.

Treatment of a patient, according to the invention, can take advantage of the migratory ability of adipose tissue derived stromal cells, and using them to provide a peptide, protein or other substance to a region of the CNS affected by a dysfunction or deficiency relating to that substance. As such, the cells of the invention may contain exogenous DNA encoding a product that is missing in an individual suffering from a CNS disorder. For example, the DNA can encode a transmitter, such as acetylcholine or GABA, or a receptor for such a transmitter. If an individual is suffering from a glutamate-induced injury, it may be desirable to introduce into the patient a gene encoding a glutamate transporting protein, which can reduce glutamate-induced cytotoxicity.

In a further approach, DNA that encodes a growth factor or a cytokine can be transfected to adipose tissue derived stromal cells, which are then administered to a patient suffering from a CNS disorder, the etiology or elaboration of which is associated with a deficit or dysfunction in the gene expression product. To this end, the invention includes, for example, the use of a gene that, upon expression, produces factors including, but are not limited to NGF, brain-derived neurotrophic factor (BDNF), glial cell line-derived neurotrophic factor (GDNF), insulin-like growth factor (IGF-1) and ciliary neurotrophic factor (CNTF). In addition, the selected gene can encode leukemia inhibitory factor (LIF) or any other of the other cytokines, disclosed, for example, by Reichardt et al. (1997, Molecular and Cellular Approaches to Neural Development, Oxford University Press:220-263), supra, that promotes cell survival or differentiation.

A therapeutic procedure according to the present invention can be effected by injecting cells, preferably stereotaxically, into the cortex or the basal ganglia. Thereafter, the diffusion and uptake of a ligand secreted by an adipose tissue derived stromal cell is beneficial in alleviating the symptoms of a disorder where the subject's neural cells are defective in the production of such a gene product. Thus, an adipose tissue derived stromal cell genetically modified to secrete a neurotrophic factor, such as nerve growth factor (NGF), is used to prevent degeneration of cholinergic neurons that might otherwise die without treatment. Alternatively, adipose tissue derived stromal cells to be grafted into a subject with a disorder characterized by a loss of dopamine neurons, such as Parkinson's disease, can be modified to contain exogenous DNA encoding L-DOPA, the precursor to dopamine.

According to the present invention, other CNS disorders likewise can be treated, including Alzheimer's disease, ganglioside storage diseases, CNS damage due to stroke, and damage in the spinal cord. For example, Alzheimer's disease is characterized by degeneration of the cholinergic neurons of the basal forebrain. The neurotransmitter for these neurons is acetylcholine, which is necessary for their survival. Engraftment of an adipose tissue derived stromal cell containing an exogenous gene encoding for a factor that would promote survival of these neurons, can be accomplished using the method of the invention described herein.

The use of adipose tissue derived stromal cells for the treatment of a disease, disorder, or a condition that affects the CNS provides an additional advantage in that the adipose tissue derived stromal cells can be introduced into a recipient without the requirement of an immunosuppressive agent. Successful transplantation of a cell is believed to require the permanent engraftment of the donor cell without inducing a graft rejection immune response generated by the recipient. Typically, in order to prevent a host rejection response, non-specific immunosuppressive agents such as cyclosporine, methotrexate, steroids and FK506 are used. These agents are administered on a daily basis and if administration is stopped, graft rejection usually results. However, an undesirable consequence in using nonspecific immunosuppressive agents is that they function by suppressing all aspects of the immune response (general immune suppression), thereby greatly increasing a recipient's susceptibility to infection and other diseases.

The present invention provides a method of administering adipose tissue derived stromal cells to a recipient having a disease, disorder, or a condition that affects the CNS without inducing an immune response by the recipient against the adipose tissue derived stromal cells. There is therefore a reduced susceptibility for the recipient of the transplanted adipose tissue derived stromal cells to incur infection and other diseases, including cancer relating conditions that are associated with immunosuppression therapy.

Genetic Modification

The cells of the present invention can also be used to express a foreign protein or molecule for a therapeutic purpose or for a method of tracking their integration and differentiation in a patient's tissue. Thus, the invention encompasses expression vectors and methods for the introduction of exogenous DNA into the cells with concomitant expression of the exogenous DNA in the cells such as those described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

The isolated nucleic acid can encode a molecule used to track the migration, integration, and survival of the cells once they are placed in the patient, or they can be used to express a protein that is mutated, deficient, or otherwise dysfunctional in the patient. Proteins for tracking can include, but are not limited to green fluorescent protein (GFP), any of the other fluorescent proteins (e.g., enhanced green, cyan, yellow, blue and red fluorescent proteins; Clontech, Mountain View, Calif.), or other tag proteins (e.g., LacZ, FLAG-tag, Myc, $His_6$, and the like) disclosed elsewhere herein. Alternatively, the isolated nucleic acid introduced into the cells can include, but is not limited to CFTR, hexosaminidase, and other gene-therapy strategies well known in the art or to be developed in the future.

Tracking the migration, differentiation and integration of the cells of the present invention is not limited to using detectable molecules expressed from a vector or virus. The migration, integration, and differentiation of a cell can be determined using a series of probes that would allow localization of transplanted adipose tissue derived stromal cells. Such probes include those for human-specific Alu, which is an abundant transposable element present in about 1 in every 5000 base pairs, thus enabling the skilled artisan to track the progress of the transplanted cell. Tracking transplanted cells may further be accomplished by using antibodies or nucleic acid probes for cell-specific markers detailed elsewhere herein, such as, but not limited to, NeuN, MAP2, neurofilament proteins, and the like.

The invention also includes an adipose tissue derived stromal cell which, when an isolated nucleic acid is introduced therein, and the protein encoded by the desired nucleic acid is expressed therefrom, where it was not previously present or expressed in the cell or where it is now expressed at a level or under circumstances different than that before the transgene was introduced, a benefit is obtained. Such a benefit may include the fact that there has been provided a system wherein the expression of the desired nucleic acid can be studied in vitro in the laboratory or in a mammal in which the cell resides, a system wherein cells comprising the introduced nucleic acid can be used as research, diagnostic and therapeutic tools, and a system wherein mammal models are generated which are useful for the development of new diagnostic and therapeutic tools for selected disease states in a mammal.

A cell expressing a desired isolated nucleic acid can be used to provide the product of the isolated nucleic acid to another cell, tissue, or whole mammal where a higher level of the gene product is useful to treat or alleviate a disease, disorder or condition associated with abnormal expression, and/or activity. Therefore, the invention includes an adipose tissue derived stromal cell expressing a desired isolated nucleic acid where increasing expression, protein level, and/ or activity of the desired protein can be useful to treat or alleviate a disease, disorder or condition involving the CNS.

The adipose tissue derived stromal cell can be genetically engineered to express a growth factor, for example NGF, prior to the administration of the engineered adipose tissue derived stromal cell into the recipient. The engineered adipose tissue derived stromal cell expresses and secretes NGF at a greater level compared with an adipose tissue derived stromal cell that has not been genetically modified to express such a factor. The increased therapeutic effect is attributed to the increase secretion of NGF from the engineered adipose tissue derived stromal cell. With the increased secretion of NGF from the engineered adipose tissue derived stromal cell, a greater amount of NGF is present for neighboring cells or distal cells to benefit from the NGF. In addition, the increase amount of NGF present in the recipient allows a decrease in the time frame in which a patient is treated.

The present invention now will be described more fully by the following examples. This invention may, however, be embodied in many different forms and should not be construed as limited to the embodiments set forth herein; rather, these embodiments are provided so that this disclosure will be thorough and complete, and will fully convey the scope of the invention to those skilled in the art.

EXAMPLES

Example 1

Hematopoietic Commitment by Adipose Tissue-Derived Stromal Cells

A. Stromal cells are isolated from human adipose tissue according to the methods described in U.S. patent application Ser. No. 09/240,029, Filed Jan. 29, 1999, now U.S. Pat. No. 6,153,432 (the contents of which are incorporated by reference), and using the modifications to the growth medium as described above. Briefly, human preadipocytes were isolated from adipose tissue removed by liposuction surgery according to the procedures previously described by Rodbell and Hauner (Rodbell (1967) and (1974); Hauner, supra). Preadipocytes from the stromal-vascular fraction were resuspended in DMEM (high glucose) media containing 10% fetal bovine serum, 5% chick embryo extract, and antibiotics and plated at 25,000 cells/well in each of the wells of a 96 well plate (150 µl/well). The cells were then placed in a 37° C. 5% $CO_2$ incubator and allowed to settle overnight. The cells are cultured as primary cultures for a period of up to 5 days following initial plating. Cells are harvested by trypsin/EDTA digestion prior to differentiation/implantation.

Human adipose tissue-derived stromal cells are tested for hematopoietic differentiation based on a bone marrow repopulation assay. Immunodeficient SCID or nude/beige mice are lethally irradiated with 11 Gy of γ-irradiation in a split dose and maintained on a diet of acidified water and autoclaved food. Hematopoietic cells from the bone marrow of the same animals are isolated at quantities of approximately $10^7$ cells per transplant hematopoietic cells of murine origin ($10^7$ bone marrow derived cells) or stromal cell human origin ($10^6$ adipose derived cells) are introduced into the mice 16 hours following the lethal irradiation by injection through the tail vein or retro-orbital vein. Alternatively, the human stromal cells are mixed with the murine hematopoietic cells at a ratio of approximately 1:10 prior to transplantation into a sublethally irradiated host animal to determine a competitive repopulation assay. Animals are transfused under methoxyflurane anesthesia. Six to twelve weeks following transplantation, blood is collected from the recipient animals and subjected to flow cytometric analysis with specific monoclonal antibodies for human hematopoietic cell markers including, but not limited to, Thy 1 (T cell marker), B220 (B cell marker), Mac 1 (macrophage marker), and HLA (H-2K, human marker). The percentage of total peripheral hematopoietic cells of human versus murine origin is determined. In similar studies, bone marrow and spleen from recipient mice are harvested and subjected to in vitro clonogenic assays for specific hematopoietic lineages. These studies utilize methylcellulose colony based assays. Cells are analyzed using comparable immunofluorescent methods for specific lineage commitment.

B. Human adipose tissue from an individual human patient is isolated by liposuction and adipose-derived stromal cells isolated in vitro according to the methods described above. The cells are cultured as primary cultures for a period of up to 5 days following initial plating in DMEM (high glucose) media containing 10% fetal bovine serum, 5% chick embryo extract, and antibiotics at 37° C. Cells are harvested by trypsin/EDTA digestion prior to differentiation/implantation.

Cells are used immediately for patients with hematopoietic disorders, such as that following high dose chemotherapy, or cryopreserved for future use in the event of an acute medical need by that patient or a histocompatible recipient. Stromal cells are infused into the recipient whether as an autologous or allogeneic transplantation, following any event such as chemotherapy or irradiation that severely compromises bone marrow function and immune competence. Stromal stem cells are marked with a fluorescent label to allow the physician to follow their fate following transplantation. Evidence of accelerated bone marrow recovery is monitored based on detection of newly synthesized hematopoietic cells (lymphoid cells, myeloid cells, erythroid cells, and platelets) in the peripheral blood stream based on flow cytometric methods.

Example 2

Astroglial Commitment by Human Adipose Tissue-Derived Stromal Cells

A. Stromal cells are isolated from human adipose tissue according to the methods described above. The cells are cultured as primary cultures for a period of up to 5 days following initial plating in a medium composed of, but not limited to, DMEM (high glucose) media containing 10% fetal bovine serum, 5% chick embryo extract, and antibiotics at 37° C. Cells are harvested by trypsin/EDTA digestion prior to differentiation/implantation.

Cells are transplanted into the central nervous system of immunodeficient mice or rats. Nude/beige or SCID mice or nude rats are anesthetized in a sealed chamber using 3% halothane in oxygen; anesthesia is maintained by intramuscular injection of 6 mg/kg of xylozine and 60 mg/kg of ketamine. The animals are transferred to a sterotaxic apparatus in a clean field. A 2-to-5-mm incision is made in the scalp 2 mm lateral to the bregma. A burr hole is made in the bone 3 mm lateral to the bregma with a dental drill. Approximately 10 µl of cell suspension (10,000 cells per µl) is injected slowly over a 30-minute period into the striatum at a depth of 4-5 mm from the surface of the brain. The wound is sutured closed and the animals followed for a period of up to 10 weeks. Animals are euthanized by intracardia perfusion following deep anesthesia with xylozine and ketamine, using ice cold PBS, 3% buffered paraformaldehyde, and then 10% sucrose. The brains are examined by immunohistochemistry and in situ hybridization for the presence of human gene markers (Alu fragment) and expression of cell lineage specific markers. Evidence of human cell survival, differentiation, and migration is determined by this approach. Modifications using cell labeling with fluorescent dyes or genetic engineering of the cells prior to implantation with viral agents can be considered.

B. Stromal cells are isolated from human adipose tissue of an individual patient for autologous or allogeneic transplantation to a histocompatible recipient according to the methods described above. The cells are cultured as primary cultures for a period of up to 5 days following initial plating in a medium composed of, but not limited to, DMEM (high glucose) media containing 10% fetal bovine serum, 5% chick embryo extract, and antibiotics at 37° C. Cells are harvested by trypsin/EDTA digestion prior to differentiation/implantation.

Stromal cells will be introduced into the central nervous system of a patient following a life-threatening and/or debilitating central nervous system disorder or disease, such as a craniovascular accident (stroke), Parkinson's disease, or Alzheimer's disease. Cells are infused into the striatum of the affected area of the brain using a neurosurgical approach. Wherever possible, radiologically guided, minimally invasive methods are used. Cognitive and metabolic function of the central nervous system are followed after the surgery to document improvements secondary to transplantation. Cells are genetically engineered with genes encoding enzymes designed to improve CNS function, such as dopamine metabolic enzymes in the case of Parkinson's disease, are used as appropriate to particular disorders.

Example 3

Neuronal Commitment by Human Adipose Tissue-Derived Stromal Cells

Improved Repair and Functional Recovery in a Traumatic Nervous System Injury

Stromal cells are isolated from human adipose tissue of an individual patient for autologous or allogeneic transplantation to a histocompatible recipient according to the methods described above. The cells are cultured as primary cultures for a period of up to 5 days following initial plating in a medium composed of, but not limited to, DMEM (high glucose) media with 1 mM glutamine but without pyruvate, containing 10% fetal bovine serum, 10% newborn calf serum, nucleoside stocks, 0.1 mM 2-mercaptoethanol, 1000 units/ml of leukemia inhibitory factor and antibiotics at 37° C.

Cells are harvested by trypsin/EDTA digestion prior to differentiation/implantation. Cells are then plated on tissue culture plastic substrate coated with 0.1% sterile gelatin solution. Cells are harvested during rapid growth stage by 0.25% trypsin and 1 mM EDTA digestion and trituration prior to differentiation/implantation. Cells are harvested as a suspension, with single cell and cell clumps together. Cells are aliquoted to 100 mm diameter bacteriological (nontissue culture) dishes in a volume of 10 ml of medium consisting of DMEM (high glucose) media with 1 mM glutamine but without pyruvate, containing 10% fetal bovine serum, 10% newborn calf serum, and nucleoside stocks (control medium). The cell cultures are maintained for 2 days, during which time cell aggregates form; at this time, medium is replaced with the original control medium. After an additional 2 days in culture (day 4 after passage), the cells are fed with control medium supplemented with all-trans retinoic acid at concentrations of between $10^{-9}$ M to $10^{-6}$ M, most preferably at $5\times10^{-7}$ M. The cells are maintained in the all trans retinoic acid supplemented medium on day 6. On day 8 after passage, the cells are ready for evaluation and use in the treatment of a spinal or peripheral nervous system traumatic injury model.

In vitro evaluation of the cells is performed by passing the cells from the bacteriological culture dish to standard tissue culture dishes to provide a substrate for attachment. Cells are allowed to adhere to the plastic and evaluated based on their morphology, consistent with a neuronal differentiation profile, and on their expression of neuronal associated proteins, including but not limited to, class III beta-tubulin, the M subunit of neurofilaments, tyrosine hydroxylase, gluatmate receptor subunits of the GluR1-4 and GluR6 classes, glial fibrillary acidic protein, myelin basic protein, and brain factor 1 (Bain et al., 1995, Develop. Biol. 168:342-357).

In vivo evaluation of the cells is performed by transplanting the cell aggregates into the syrinx that forms around an experimentally induced thoracic spinal cord lesion in rats (McDonald et al., 1999, Nature Med. 5:1410-1412). The thoracic spinal cord injury model (thoracic vertebra 9-10) is created in Long-Evans rats using a 10 gram rod 2.5 mm in diameter falling 25 mm. On the ninth day after the injury, adipose tissue-derived stromal cell aggregates (approximately $10^6$ cells) are transplanted by injection using a microstereotaxic injection system into the syrinx of the thoracic spinal cord injury. Sham operated controls are injected with an equivalent volume of media alone (no cells). Beginning on the day of transplantation, rats receive cyclosporine daily (10 mg/kg) to prevent rejection. Hindlimb motor function is assessed based on the Basso-Beattie-Breesnahan Locomotor Rating Scale in the rats over a 6 week period following transplantation to allow functional comparison of the recovery between stromal cell transplanted and sham operated controls. At the conclusion of the study (6 weeks), animals are sacrificed and the tissues examined histologically for evidence of human adipose stromal cells are detected based on in situ detection of the human Alu DNA. Cell differentiation is determined by antibody detection of oligodendrocyte specific markers such as, but not exclusively, adenomatous polyposis coli gene product APC CC-1, astrocyte specific markers such as, but not exclusively, glial fibrillary acidic protein, GFAP, and neuronal such as, but not exclusively, neuron-specific nuclear protein, NeuN. Colocalization of the Alu DNA with differentiation specific markers is taken as evidence of stromal cell differentiation.

Alternatively, the isolated adipose tissue derived stromal cells are cultured as primary cultures for a period of up to 5 days following initial plating in a medium composed of, but not limited to, DMEM (high glucose) media containing 10% fetal bovine serum, 5% chick embryo extract, and antibiotics at 37° C. Cells are harvested by trypsin/EDTA digestion prior to differentiation/implantation.

Human adipose tissue-derived stromal cells are tested for neuronal differentiation based on in vitro assays. Human adipose tissue-derived stromal cells are cultured at concentrations of 8,000 cells/cm$^2$ for 24 hours in DMEM supplemented with 20% fetal bovine serum and antibiotics. The cells are then treated with antioxidants such as BHA at concentrations of 20 µM to 200 µM in DMEM with 0% fetal bovine serum for periods of 5 hours to 5 days. Cells are fixed and examined for the expression of neuronal differentiation by (a) morphological criteria; (b) immunohistochemical, immunofluorescent or flow cytometric criteria; (c) immunoblot criteria; and/or (d) polymerase chain reaction or northern blot analysis of selected mRNAs. Cells are assessed for their expression of a subset of the following neuronal markers: NeuN, NF-M, NSE, nestin, and trkA using antibody or oligonucleotide reagents. Morphologic criteria of differentiation include the formation of a contracted multipolar cell body with membranous, process-like cell extensions leading to growth cone-like termini and filopodial extensions, the ability of such cells to generate and maintain an action potential consistent with neuronal signal transmission, and the ability to express receptors and uptake systems for known neurotransmitters, such as the glutamate.

Example 4

Hepatocyte Commitment by Human Adipose Tissue-Derived Stromal Cells

A. Stromal cells are isolated from human adipose tissue according to the methods described in "Methods and Composition for the Differentiation of Human Preadipocytes into Adipocytes" Ser. No. 09/240,029, Filed Jan. 29, 1999, now U.S. Pat. No. 6,153,432 and using the modifications listed above. The cells are cultured as primary cultures for a period of up to 5 days following initial plating in a medium composed of, but not limited to, DMEM (high glucose) media containing 10% fetal bovine serum, 5% chick embryo extract, and antibiotics at 37° C. Cells will be harvested by trypsin/EDTA digestion prior to differentiation/implantation.

Adipose tissue-derived stromal cells are transplanted into immunodeficient nude mice carrying a transgene for the mouse major urinary protein-urokinase-type plasminogen activator fusion gene (Weglarz T C, Degen J L, Sandgren E P 2000 Hepatocyte transplantation into diseased mouse liver: kinetics of parenchymal repopulation and identification of the proliferative capacity of tetraploid and octaploid hepatocytes. Am J. Pathol 157:1963-1974). These animals exhibit a progressive degeneration of the liver. The stromal cells are introduced into the animal model by transplantation into the spleen, intraperitoneal, and/or intravenous infusion. Representative animals from control or experimental groups are sacrificed at intervals over a 4 month time course. Evidence of liver regeneration will be assessed based on histologic and molecular biological analyses of the liver tissue. Immunohistochemical and molecular biological (Alu staining) methods will document the presence of human cells in the regenerated liver.

B. Stromal cells will be isolated from human adipose tissue of an individual patient for autologous or allogeneic transplantation to a histocompatible recipient according to the methods described in "Methods and Composition for the Differentiation of Human Preadipocytes into Adipocytes" Ser. No. 09/240,029, Filed Jan. 29, 1999, now U.S. Pat. No. 6,153,432 and using the modifications listed above. The cells are cultured as primary cultures for a period of up to 5 days following initial plating in a medium composed of, but not limited to, DMEM (high glucose) media containing 10% fetal bovine serum, 5% chick embryo extract, and antibiotics at 37° C. Cells will be harvested by trypsin/EDTA digestion prior to differentiation/implantation.

Stromal cells will be introduced into the spleen, circulation, and/or peritoneum of a patient suffering from degenerative liver diseases of any origin, secondary to viral infection, toxin ingestion, or inborn metabolic errors. Wherever possible, radiologically guided, minimally invasive methods will be used to implant the cells. Cells genetically engineered with genes encoding enzymes designed to improve hepatic function will be used as appropriate to particular disorders.

Example 5

Characteristics of BMSCs and ASCs

The following experiments were designed to establish that the rat was an appropriate animal model for stroke since the therapeutic efficacy of human adipose tissue derived stromal/stem cells (ASCs) and BMSCs can be tested in a rat stroke model using rat ASCs and BMSCs. The phenotype and differentiation potential of rat cells was evaluated to determine their similarity to human cells. ASCs and BMSCs were isolated from Fisher rats and expanded by culture for 4 passages. ASCs and BMSCs were also isolated from transgenic rats expressing the human heat stable alkaline phosphatase (AP). These AP-ASCs and AP-BMSCs were also expanded to P4. The cells were characterized by flow cytometry at passage four (P4) for expression of several stromal and other cell surface markers that define both human ASCs and BMSCs. Table 1 indicates that rat ASCs and BMSCs display a similar phenotype relative to their human counterparts. The cells do not express hematopoeitic markers but express high levels of some stromal markers. Furthermore the AP-ASCs and AP-BMSCs were phenotypically similar to normal rat ASCs and BMSCs respectively.

TABLE 1

Phenotype of Human and Rat ASCs and BMSCs (P4) (% Positive Cells)

| Cluster | hASC* | rASC¶ | rAP-ASC† | hBMSC‡ | rBMSC¶ | rAP-BMSC† |
|---|---|---|---|---|---|---|
| CD11b/c | 3.1 ± 3.9** | <0.01 | <0.01 | 0.01 | <0.01 | <0.01 |
| Mphage | 0.2 ± 0.2 | 4.6 | 4.3 | 0.01 | 4.3 ± 1.9 | 12.1 |
| CD29 | 94.7 ± 2.05 | 96 | 77 | 86.7 | 97.2 ± 0.7 | 98 |
| CD31 | 21 ± 19.9 | <0.01 | 0.9 | Neg | <0.01 | <0.01 |
| CD45 | 0.9 ± 0.7 | <0.01 | 0.3 | 0.01 | <0.01 | <0.01 |
| CD54 | 81.9 ± 14.1 | 79 | 94.4 | 96.4 | 72.7 ± 14.8 | 31.3 |
| CD63 | 66.1 ± 25.1 | 87.1 | 91.9 | 68.4 | 74.3 ± 17.1 | 76.9 |
| CD73 | 94.2 ± 4.2 | 87.7 | 95.6 | 89.2 | 91.2 ± 4.4 | 84.4 |
| CD90 | 97.2 ± 1.0 | 97.2 | 92.7 | 93.1 | 98.2 ± 0.4 | 98.5 |
| Class I | 92.4 ± 6.3 | 37.3†̄ | 45.8†̄ | 93.5 | 38.3 ± 29.6†̄ | 12.5†̄ |
| Class II | 2.2 ± 2.5 | <0.01 | 0.2 | 0.1 | <0.01 | <0.01 |

*n = 5;
**CD11a;
†n = 1;
‡n = 1–4;
¶n = 4;
†̄Dim median flourescence intensity with most cells being positive.

Both ASCs and BMSCs can be obtained from normal adults relatively easily and without ethical controversy. A characteristic that is advantageous for therapeutic purposes is the fact that both ASCs and BMSCs do not induce alloreactive immune responses upon transplantation. Several studies have shown that in addition to being non-immunogenic, BMSCs can actively suppress ongoing immune responses in vitro and in vivo, making them an excellent alternative to autologous cell transplantation. It was also observed that human ASCs did not provoke alloreactive T cell responses and shared similar immunosuppressive properties with BMSCs. A comparison of ASCs and BMSCs demonstrated that ASCs were superior in maintenance of proliferation potential and their capacity to differentiate. Microarray analysis revealed that although the gene expression profiles of ASCs and BMSCs were highly similar, there was a small percentage of differentially expressed genes. Some of those genes expressed at higher levels in ASCs were identified to be involved in the regulation of proliferation of stem cells. Another group showed that Rhesus ASCs had higher neurogenic potential, but lower osteogenic potential when compared to Rhesus BMSCs. Without wishing to be bound by any particular theory, it is believed that the small dissimilarities between the two cell types could translate to differences in their therapeutic potential in treatment of stroke. Both ASCs and BMSCs have the potential to express neuronal and glial marker proteins when treated with neurogenic factors in vitro (Safford et al., 2002, Biochem Biophys Res Commun. 294:371-379; Woodbury et al., 2000, J Neurosci 61:364-370) although only a very small fraction of ASCs and BMSCs was observed to express neuronal markers when they were injected into brains of normal or injured adult animals.

Therapeutic Effect of Stromal Cells in Stroke:

When BMSCs were delivered intravenously (IV) to rats that have undergone stroke or have otherwise been subjected to middle cerebral artery occlusion MCAo, the administered cells migrated to and targeted the area around the ischemic lesion with relatively minimal migration to the unaffected contralateral hemisphere. The reduction in cerebral blood flow following ischemic stroke causes a dynamic inflammatory process. This complex set of interactions involves both resident immune function cells and molecules as well as the damaged cells of the brain itself. The acute local reaction is followed by stimulation of neighboring endothelial cells to produce adhesion molecules that causes migration of peripheral circulating leukocytes. The chemokine SDF-1, for example, has been demonstrated to be upregulated and principally localized to the ischemic penumbra post MCAo (Hill et al., 2004, J. Neuropathol Exp Neur 63:84-96). Without wishing to be bound by any particular theory, it is believed that these same changes may affect the migration of the BMSCs or ASCs delivered for therapeutic purposes and their targeting to the site of injury. Since the damaged brain undergoes changes that are time dependent, the signals attracting ASCs or BMSCs may be strongest within a specific time window after the initiation of stroke. Using micro-chemotaxis chambers, human BMSCs were shown to be attracted to ischemic brain extracts from post MCAo-day 1, 2 and 7 (Wang et al., 2002, Exp Hematol 30:831-6). Cytokines MCP-1, MIP-1 and IL-8 that are up-regulated in ischemic brain lesions also attracted BMSCs.

Induction of Neurorestorative Pathways

Treatment of rats subjected to permanent MCAo with BMSCs dramatically enhanced the proliferation of neural progenitors as well as migratory neuroblasts in the subventricular zone adjacent to the ischemic lesion and the ischemic boundary zone (Zhang et al., 2004, J Neurosci. 24:5810-5). In addition, increased axonal density, enhanced proliferation of glial and neural progenitors and reduced glial scarring were observed in the subventricular zone and penumbra region of the lesion as long as 4 months after treatment of stroked-rats treated with BMSCs (Li et al., 2005, Glia. 49:407-17). These changes are believed to be brought about by the production of neurotrophic or other factors by the BMSCs which in turn may be affected by factors present in the ischemic tissue. Both ASCs and BMSCs secrete several factors that play a role in angiogenesis, neurogenesis and proliferation of progenitor cells. These include among others, VEGF, BDNF, NGF, HGF and LIF. It was observed that human ASCs secrete greater than two fold higher levels of VEGF compared to human BMSCs in culture. ASCs and BMSCs may also differ in the secretion of other beneficial cytokines. The production of these factors by these cells is enhanced under conditions of ischemia and hypoxia. For example culturing BMSCs with ischemic brain extracts enhanced the production of VEGF, BDNF, NGF and HGF. ASCs exposed to hypoxia produced 5-fold more VEGF relative to BMSCs and conditioned medium from hypoxic ASCs significantly enhanced endothelial cell growth and reduced endothelial cell apoptosis (Rehman et al., 2004, Circulation. 109:1292-8). It has been shown that human BMSCs promote proliferation of human neural stem cells (NSCs) in both contact dependent and independent ways. It has also been observed that BMSCs enhance neural differentiation of NSCs.

Alkaline Phosphatase Expression in AP-BMSCs and AP-ASCs

Transgenic rats expressing heat stable human placental alkaline phosphatase (AP) are useful for identifying AP positive cells in migration studies. AP positive cells isolated from the transgenic rats are also useful for tracking cells following transplantation into a recipient. It has been observed that glial progenitor cells isolated from these rats were easily located following transplantation into a rat model of spinal cord injury and the morphology and differentiation of these cells in the spinal cord were easily evaluated by histochemistry and immunochemistry for human AP expression. AP-ASCs and BMSCs were isolated from the AP rats and cultured through 1-4 passages. To confirm AP-expression, AP-cells were plated in chamber slides and allowed to adhere for one to two days. Cells were stained in the chamber slides for AP enzyme activity using Nitro Blue Tetrazolium/5-Bromo-4-Chloro-3-Indolyl Phosphate (NBT-BCIP) substrate using methods known in the art. Prior to final mounting of the slide, the nuclei of the cells were labeled with (DAPI). As seen in FIG. 1, the AP-cells stained positive for AP and thereby confirming the expression of AP in the cells. Control (wild type) cells were negative for AP. All nuclei stained positive with the DAPI dye.

Behavioral Recovery after Allogeneic Transplantation of Rat BMSCs after MCAo

Figure 2A:
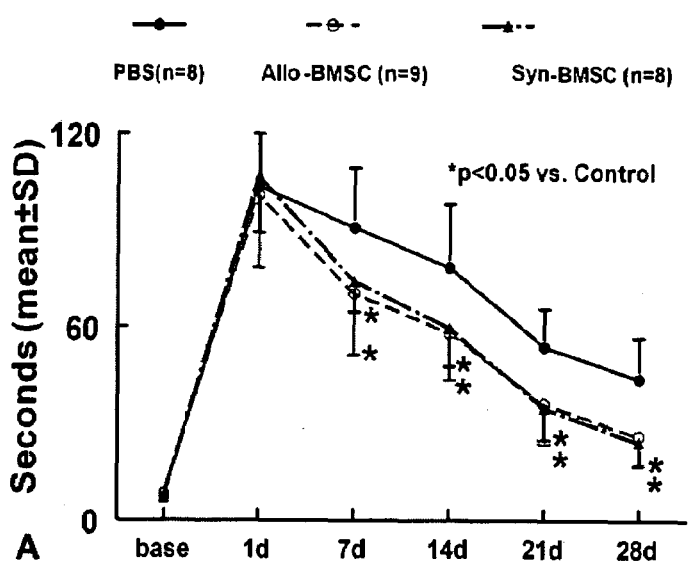
FIG. 2A through FIG. 2C, is a series of graphs depicting the temporal profile of functional recovery in PBS control and BMSC (allogeneic and syngeneic) treated rats subjected to 2 hour middle cerebral artery occlusion (MCAo).
Figure 2B:
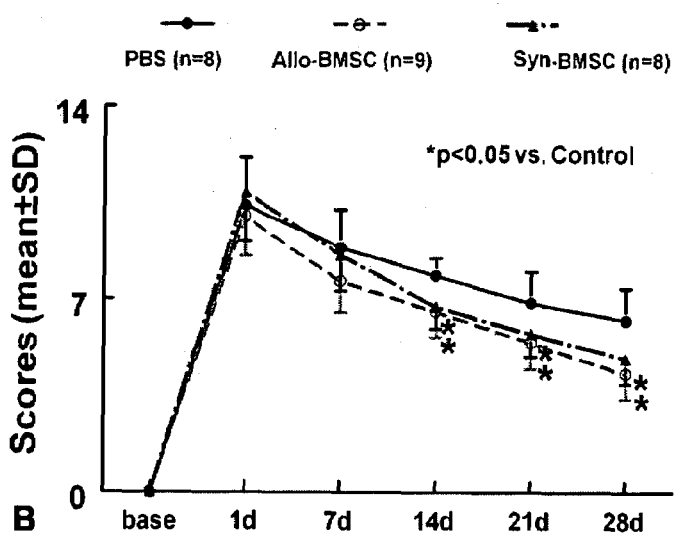
Figure 2C:
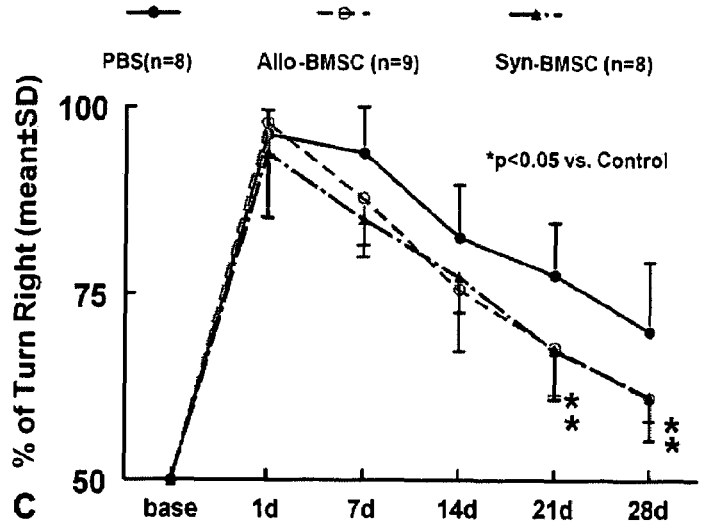

The next set of experiments were designed to investigate the effects of allogeneic (allo-) and syngeneic (syn-) rat BMSCs (rBMSC) in rats subjected to stroke. These studies have particular importance with respect to the development of a commercial "off the shelf" product that can be used in emergency clinical settings. Adult rats were subjected to 2 hours of middle cerebral artery occlusion (MCAo). At 24 hours after MCAo, rats were injected intravenously with phosphate buffered saline, allo-rBMSCs ($3 \times 10^6$/rat) or syn-rBMSCs ($3 \times 10^6$/rat). Measurements of neurological functional recovery were performed. Rats were sacrificed at 28 days after treatment. Significant functional recovery (P<0.05) was found in both groups treated with rBMSCs compared to non-treated (PBS) MCAo controls; however, no difference was detected between allo- and syn-rBMSC treated rats (FIG. 2).

Neurological function evaluated as follows:

A: Adhesive-removal patch test: Two small pieces of adhesive-backed paper dots of equal size (113.1 mm 2) were used as bilateral tactile stimuli occupying the distal-radial region of each forelimb. The time to remove each stimulus from forelimbs was recorded on 5 trials per day. Individual trials were separated by at least 5 minutes. Before surgery, the animals were trained for 3 days. Once the rats were able to remove the dots within 10 seconds, they were subjected to MCAo.

B: Modified neurological severity score (mNSS): mNSS is a composite of motor, sensory, balance and reflex tests. Neurological function was graded on a scale of 0 to 18 (normal score 0; maximal deficit score 18). In the severity scores of injury, one score point was awarded for the inability to perform the test or for the lack of a tested reflex; thus, the higher score, the more severe is the injury.

C: Corner test: A rat was placed between two attached boards. The edges of the two boards were at a 30° angle with a small opening along the joint to encourage entry into the corner. The rat was placed facing and half way to the corner. When entering deep into the corner, both sides of the vibrissae were stimulated together. The rat then reared forward and upward, and then turned back to face the open end. A non-injured rat either turned left or right, but the injured rats preferentially turned toward the non-impaired side. The turns in one versus the other direction were recorded from ten trials for each test, and the fraction of the turns was used as the corner test score.

Example 6

Comparative Evaluation of ASC and BMSC Efficacy in a Rat Model of Stroke

Permanent middle cerebral artery occlusion (MCAo) are performed in aged rats (18 months old) to induce stroke. Different doses of BMSCs or ASCs or vehicle are delivered intravenously after stroke. Culture expanded AP-BMSCs or ASCs are cryopreserved until time of injection. One day after MCAo, the cells are thawed. The viability is measured by counting cells with Trypan Blue exclusion dye on a hemocytometer. Cells of at least 80% viability are used. The cells are resuspended in PBS to result in the desired dose per 1 ml. The cell suspension is delivered through the tail vein at a steady and slow rate. Standardized neurological behavior tests are performed at various intervals to assess sensory and motor functions. Dose-dependent improvement in the functional behavior after treatment with ASCs or BMSCs are evaluated compared to PBS treated animals. Statistical evaluation is performed to compare ASCs with BMSCs. One month after treatment, animals are re-anesthetized with ketamine (44 mg/kg) and xylazine (13 mg/kg). Rat brains are fixed by transcardial perfusion with saline, followed by perfusion with saline and 4% paraformaldehyde. The brains are cryoprotected in 30% sucrose and then processed for frozen sections. The cerebral tissues are sectioned into six equally spaced (2 mm) coronal blocks. A series of adjacent 15-20-μm-thick sections are cut from each block in the coronal plane and stained for AP as described elsewhere herein. Endogenous AP is heat inactivated at 60° C. for 1 hour leaving the heat stable human AP of transplanted cells intact. Under microscopy, the distribution of cells in and around the infarct are evaluated. One section per 2 mm block is examined and distribution of AP-positive cells is examined in the entire section. The number of AP-positive cells in and around the ischemic lesion is counted using imaging software. The data are analyzed to determine dose-dependent and cell dependent differences. Double immunostaining for human AP and neuronal (MAP2, Tuj1) or glial proteins (GFAP, RIP) is performed on representative sections to assess possible differentiation of transplanted cells. The Experimental design is summarized in Table 2.

TABLE 2

| Cell dose | Rat AP-ASC No. of rats | Rat AP-BMSC No. of rats | Vehicle No. of rats | Neurological testing (Days after stroke induction) | Time of injection/ Time of sacrifice |
|---|---|---|---|---|---|
| 0 | | | 20 | d0, d1, d7, d14, d21, d30 | 1 d/1 m |
| $1 \times 10^6$ | 20 | 20 | | d0, d1, d7, d14, d21, d30 | 1 d/1 m |
| $3 \times 10^6$ | 20 | 20 | | d0, d1, d7, d14, d21, d30 | 1 d/1 m |
| $10 \times 10^6$ | 20 | 20 | | d0, d1, d7, d14, d21, d30 | 1 d/1 m |

Therapeutic effect from transplantation of the cells in the rat MCAo model can be tested using a number of neurological tests. Neurological tests encompass a battery of tests including fore limb flexion, torso twisting, hind limb placement, gait disturbances and wide wall walk balance test. Each test is scored on set of points and the total score is used to assess the severity of the stroke. Table 3 represents control data from 171 rats 23 hours after MCAo induced stroke.

TABLE 3

| Test | Avg | STD |
|---|---|---|
| Fore limb flexion | 0.74 | +/−0.27 |
| Torso twist | 1.29 | +/−0.49 |
| Hind limb | 0.74 | +/−0.31 |
| Gait disturbances | 1.89 | +/−0.76 |
| Wall walk | 4.42 | +/−1.82 |
| Total score | 9.09 | +/−2.76 |

Without wishing to be bound by any particular theory, it is believed that the total neurological score corresponds to the following qualitative description of stroke severity:

5.01-7.00 Low Medium stroke;
7.01-10.00 High Medium stroke;
10.01-13.00 Severe stroke.

Statistical analysis is performed to validate the stroke studies. A sample size of 20 rats per treatment group allow for the detection of about 30% improvement after cell injection, using a 5% significance level with 86% power. A 2-sample t-test can be used for this power calculation. The "day0" (before MCAo) measurement is used as the baseline value. The change from baseline in the total score can be calculated for each rat and each post-injection time point. The following comparisons can be performed using an Analysis of Covariance (ANCOVA) model.

To compare ASCs with BMSCs at each post-injection time point, the following procedure is used: Combine the three cell doses within each cell type, then compare the change from baseline in the total score at each post-injection time point using an ANCOVA model with cell type, dose, and cell type-by-dose interaction as factors covarying on the baseline score. If the cell type-by-dose interaction is not statistically significant based at the significance level of 0.1, the interaction term is dropped in the final model. The least squares mean for the difference in the two cell types can be assessed. The 95% confidence interval for the difference in the two cell types is applied.

To compare ASCs with BMSCs over time, the following procedure is used: A repeated measures analysis of variance (ANOVA) is used to test the difference of total score between ASCs and BMSCs. In this ANOVA model, the total score is the dependent variable, and cell type, dose, and cell type-by-dose interaction is the independent variables.

To compare each dose with the vehicle alone group, the following procedure is used: Combine all 7 treatment groups and compare the change from baseline in the total score at each post-injection time point using an ANCOVA model with treatment (vehicle alone, ASCs and BMSCs), dose, and treatment-by-dose interaction as factors covarying on the baseline score. Pair-wise comparison for each dose versus vehicle can be performed. Multiple comparison adjustment is not performed. If the interaction term is not statistically significant based at a significance level of 0.1, the interaction term is dropped in the final model. The least squares mean for the difference in each of 6 pair-wise comparisons is assessed. The 95% confidence interval for each of the 6 differences is applied determined.

In addition, within each rat's data a regression line is generated for the total score over the 5 time points. The slope is estimated for each rat. The mean slopes is compared between the 2 cell types and between each of the 6 doses and the placebo treatment group. is comparison is performed using an ANOVA model with above-mentioned factors.

Example 7

BMSCs or ASCs Migrate to the Ischemic Site where they Influence Endogenous NPCs and Promote Plasticity of the Tissue Without wishing to be bound by any particular theory, it is believed that selective migration of BMSCs to the site of injury is influenced by signals generated in the damaged tissue. These signals may vary with time based on the temporal changes ongoing in the dying neural tissue which defines a time window for attraction and/or survival of ASCs and BMSCs at the injury site. The ability of ASCs or BMSCs to target ischemic sites can be investigated in vitro using brain extracts from stroked rats (ischemic brain extract, IBE) and measuring the migration of cells across a porous membrane (8 micron) coated with basement membrane such as Matrigel towards the extracts (BD Biocoat Matrigel Invasion chambers). The experimental design is summarized in Table 4. IBE is generated from rat brains subjected to MCAo as follows. Experimental rats are sacrificed at various points after stroke. The forebrain tissues are removed and placed on ice. The ipsilateral hemisphere of stroked and control (normal) rats are dissected, rapidly weighed and homogenized in IMDM at 150 mg tissue/ml. The homogenate is centrifuged at 100,000 g for 20 minutes at 4° C. and the supernatant removed and stored at −80° C.

The optimal seeding density of ASCs or BMSCs in the culture insert can be determined using a positive control such as a chemokine, SDF1α or MIP1α or a combination of both. The optimal time of migration can also be determined. Control culture inserts of the same pore size but without matrigel is performed in parallel. Cells migrating to the under side of the membrane are stained and counted. 3-5 fields per membrane are counted including areas in the center and periphery. The number of cells/average field of view can be determined. While migration through uncoated pores shows the attraction of BMSCs or ASCs to chemoattractants in ischemic brain extracts (IBE), significant migration through matrigel demonstrates the ability of the cells to invade basement membrane and indicate their ability to leave the vasculature and enter the brain. Differences in the extent of migration of ASCs versus BMSCs as well as in the intensity of the response to IBE obtained at different time points can be determined.

Example 8

Treatment of Stroke with Intravenous Administration of ASCs

Rats are subjected to middle cerebral artery occlusion (MCAo) for a period of time using the intraluminal occlusion model. Following MCAo, the control group (rats subjected to MCAo without receiving ASCs) is compared with the experimental groups, which include delivery of ASCs intravenously at 24 hours after MCAo; phosphate buffered saline (PBS) control; and ASCs cultured in neuronal differentiation medium. For intravenous administration of ASCs, a femoral vein is cannulated and either $1.5 \times 10^6$, $3 \times 10^6$ or $10 \times 10^6$ ASCs are injected into the vein.

To perform behavioral and immunohistochemistry tests, each rat is subjected to a series of behavioral tests (NSS and adhesive removal test) to evaluate neurological function before MCAo, and at 1, 4, 7 and 14 days after MCAo. Single and double immunohistochemistry assays are employed to identify cell specific proteins of BrdU reactive ASCs.

The effects of ASCs injected via different routes (intraarterial versus intravenous) after stroke in rats can be evaluated. Comparative studies can be performed to assess the effects of ASCs injected via IA or IV on neurological function, neurogenesis, and angiogenesis in ischemic rats. Rats are subjected to middle cerebral artery occlusion (MCAo) for two hours. After 24 hours, $1.5 \times 10^6$, $3 \times 10^6$ or $10 \times 10^6$ ASCs or phosphate buffered saline control are infused into the carotid artery or the tail vein of the rat. The rats (IA and IV injected) are sacrificed at day one, day seven, day fourteen and day twenty eight after cell injection; whereas the control rats are sacrificed at day twenty eight after PBS injection. Behavioral tests (an adhesive-removal test and a modified Neurological Severity Score, mNSS) are performed at 1, 7, 14, 21 and 28 days after MCAo. BrdU immunohistochemistry is used to evaluate

TABLE 4

| Cells in Upper Chamber | Brain Extracts in Lower chamber | | | | | |
|---|---|---|---|---|---|---|
| | Normal Ext | Ischemic D1 Ext | Ischemic D2 Ext | Ischemic D7 Ext | Ischemic D14 Ext | Ischemic D30 Ext |
| ASC | N = 5 | N = 5 | N = 5 | N = 5 | N = 5 | N = 5 |
| BMSC | N = 5 | N = 5 | N = 5 | N = 5 | N = 5 | N = 5 | endogenous neurogenesis in both the subventricular zone (SVZ) and the subgranular zone (SGZ). Immunohistochemistry is employed to measure angiogenesis in the ischemic boundary zone (IBZ).

An observed recovery from conditions of stroke as measured by the adhesive-removal test and mNSS in both IA and IV groups indicates a therapeutic effect. Rats receiving ASCs both by IA and IV are expected to exhibit recovery from conditions of stroke by day seven and persist to at least day twenty eight after cell injections compared with control mammals that did not receive injection of ASCs. Immunohistochemistry results showing a significant increase in the number of BrdU positive cells in the SVZ and SGZ during 7-14 days after stroke and returning to baseline at day twenty eight is also an indication of a therapeutic outcome.

Quantitative analysis using immunohistochemistry techniques can be performed to assess angiogenesis resulting from the ASC administration. Angiogenesis is expected to persist for at least day twenty eight in the IBZ after the onset of stroke. It is believed that delivery of ASCs to the ischemic brain through both intracarotid and intravenous routes provide therapeutic benefits after stroke.

Example 9

Treatment of Stroke in Rats with Human Bone Marrow Stromal Cells

The experiments presented herein address whether treatment of stroke in rats using xenogeneic human ASCs (hASCs) necessitates the use of an immunosuppressive agent, for example, cyclosporin A (CsA), and whether CsA affects the neurological response to stroke and treatment with hASC in rats. hASCs are obtained from three healthy human donors. Adult rats are subjected to 2 hours of middle cerebral artery occlusion (MCAo). Four groups of ischemic rats are subjected to: 1) MCAo alone without treatment; 2) 15 mg/kg CsA by gastric feeding daily beginning at one day after MCAo for 27 days; 3) tail intravenous injection of $1.5 \times 10^6$, $3 \times 10^6$ or $10 \times 10^6$ hASCs at one day after MCAo; and 4) co-treatment with hASCs and CsA after MCAo. Functional outcome is measured by using an adhesive-removal patch test and a modified Neurological Severity Score (mNSS) before stroke and at 1, 7, 14, 21 and 28 days after stroke. A human-specific antibody (Mab1281) against cellular nuclei is used to identify hASCs within the brain tissue. Since unwanted activation of T-lymphocytes promotes graft rejection, human graft-versus-rat host cytotoxic T lymphocyte (CTL) response is measured using a $^{51}$Cr assay to determine the lytic effect. It is believed that hASCs do not induce a CTL response both in vitro and in vivo, and therefore CsA immunosuppression is not needed as an adjunctive therapy when administering hASCs to a rat.

Example 10

Allogeneic Rat ASCs Promote Brain Remodeling without Immunologic Sensitization in Stroked Rats The experiments presented herein address the effects of allogeneic (allo-) and syngeneic (syn-) rat ASCs for the treatment of stroke with respect to functional outcome based on immune reaction, glial scar formation and glial-axonal architecture. Rats are subjected to middle cerebral artery occlusion (MCAo) for two hours. At 24 hours after MCAo, rats are injected intravenously with phosphate buffered saline (PBS, n=8), syngeneic rat strain ASCs ($1.5 \times 10^6$, $3 \times 10^6$ or $10 \times 10^6$ ASCs), or allogeneic rat strain ASC ($1.5 \times 10^6$, $3 \times 10^6$ or $10 \times 10^6$ ASCs). Neurological functional recovery can be performed using the Neurological Severity Score, adhesive-removal patch and Corner tests. Rats are sacrificed at day twenty eight after treatment, and are bled to determine antibody titers to the injected ASCs. Lymphocytes collected from mesenteric and cervical lymph nodes are cultured with irradiated syn- or allo-spleen cells to determine T cell proliferative responses against donor alloantigens using the Mixed Lymphocyte Reaction assay. Antibody titers to ASCs are determined by a flow cytometry method. In situ hybridization and double immunostaining techniques are employed for male Y-chromosome$^+$ bearing ASCs and brain cell type identification.

Significant functional recovery found in both groups treated with ASC (syn- or allo-) compared to PBS controls, and no difference between syn- and allo-ASC treated rats is an indication of a therapeutic outcome for allogenic cells. It is believed that both syn- and allo-ASCs are useful in the treatment of stroke in rats and contribute to improve neurological recovery and enhance brain remodeling with no indication of immunologic sensitization.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The disclosures of each and every patent, patent application, and publication cited herein are hereby incorporated herein by reference in their entirety.

What is claimed is:

1. A method of treating a mammal suffering from a disease, disorder or condition of the central nervous system, wherein said disease, disorder or condition is selected from the group consisting of an ischemic induced injury, a spinal cord injury, and stroke, the method comprising administering an adipose tissue derived stromal cell to the central nervous system of said mammal, wherein the presence of said stromal cell in the central nervous system effects treatment of said disease, disorder or condition.

2. The method of claim 1, wherein said stromal cell is selected from the group consisting of an autologous stromal cell, an allogeneic stromal cell, and a syngeneic stromal cell with respect to said mammal.

3. The method of claim 1, wherein said stromal cell is derived from a human donor.

4. The method of claim 1, wherein said mammal is a human.

5. The method of claim 1, wherein said disease, disorder or condition is injury to a tissue or a cell of said central nervous system.

6. The method of claim 1, wherein said disease, disorder or condition is within the brain of said mammal.

7. The method of claim 1, wherein prior to administering said stromal cell, said stromal cell is cultured in vitro for a period of time to differentiate into a cell that expresses at least one protein characteristic of a neuronal cell.

8. The method of claim 1, wherein said stromal cell is administered to said mammal by a route selected from the group consisting of intravascular, intracerebral, parenteral, intraperitoneal, intravenous, epidural, intraspinal, intrasternal, intra-articular, intra-synovial, intrathecal, and intra-arterial.

9. The method of claim 1, wherein said stromal cell in the central nervous system of the mammal secretes a factor selected from the group consisting of a growth factor, a trophic factor and a cytokine.

10. The method of clam 1, wherein said stromal cell is administered to said mammal at the site of injury.

11. The method of clam 1, wherein said stromal cell is administered to said mammal at an adjacent site to the site of injury.

12. The method of claim 11, wherein following administering said stromal cell to said mammal, said stromal cell migrates to the site of injury.

13. The method of claim 1, wherein said stromal cell in the central nervous system activates the differentiation of neighboring cells.

14. The method of claim 1, wherein said stromal cell in the central nervous system expresses at least one protein characteristic of a cell of the central nervous system.

15. The method of claim 14, wherein said stromal cell expresses at least one protein characteristic of a cell of the central nervous system selected from the group consisting of class III β-tubulin, the M subunit of neurofilaments, tyrosine hydroxylase, glutamate receptor subunits of the GluR1-4 and GluR6 classes, glial fibrillary acidic protein, myelin basic protein, brain factor 1, NeuN, NF-M, NSE, nestin, and trkA.

16. The method of claim 1, wherein said stromal cell is administered concomitantly with at least one factor selected from the group consisting of atrophic factor, a growth factor, a cytokine, a neurotrophin, or any combination thereof.

17. The method of claim 1, where said stromal cell is administered to the mammal in the absence of an immunosuppressive agent.

* * * * *